US006881567B2

(12) United States Patent
Boyetchko et al.

(10) Patent No.: US 6,881,567 B2
(45) Date of Patent: Apr. 19, 2005

(54) PRE-EMERGENT BIOLOGICAL CONTROL AGENTS

(75) Inventors: Susan M. Boyetchko, Saskatoon (CA); Karen Sawchyn, Saskatoon (CA); Jon Geissler, Saskatoon (CA)

(73) Assignee: Her Majesty the Queen in Right of Canada as Represented by the Minister of Agricultural and Agri-Food Canada, Saskatchewan (CA)

( * ) Notice: Subject to any disclaimer, the term of this patent is extended or adjusted under 35 U.S.C. 154(b) by 300 days.

(21) Appl. No.: 10/100,569

(22) Filed: Mar. 15, 2002

(65) Prior Publication Data

US 2003/0054959 A1 Mar. 20, 2003

Related U.S. Application Data

(60) Provisional application No. 60/276,413, filed on Mar. 16, 2001.

(51) Int. Cl.[7] .............................. C12N 1/20; A01C 1/00; A01N 63/00
(52) U.S. Cl. ..................... 435/252.34; 504/117; 47/58.1
(58) Field of Search .......................... 47/58.1, 58.1 SC; 435/252.34, 262, 267, 874–77; 504/117, 116.1; 414/93.47, 93.3, 780; 424/93.47, 93.3, 780

(56) References Cited

U.S. PATENT DOCUMENTS

| 4,606,751 A | 8/1986 | Van Dyke et al. ............... 71/79 |
| 5,030,562 A | 7/1991 | Elliott et al. ................... 435/29 |
| 5,074,902 A | 12/1991 | Connick, Jr. et al. ............ 71/79 |

(Continued)

FOREIGN PATENT DOCUMENTS

| EP | 0 839 449 A1 | 5/1998 |
| JP | 10179139 | 7/1998 |
| WO | WO 91/03161 | 3/1991 |
| WO | WO 98/05213 | 2/1998 |
| WO | WO 98/08389 | 3/1998 |

OTHER PUBLICATIONS

Atlas R., Park L. (Eds.) 1993, Handbook of Microbiological Media, CRC Press, Boca Raton, FL. USA p. 529.
Beckie, H.J., A. Legere, A.G. Thomas, L.T. Juras, and M.D. Devine, 1996 Survey of Herbicide–Resistant Wild Oat and Green Foxtail in Saskatchewan: Interim Report. AAFC Report, 22 pp.).
Boyetchko, S. M., "Efficacy of Rhizobacteria as Biological Control Agents of Grassy Weeds," p. 460–465, In: Proceedings of the Soils and Crop Workshop '97, Saskatoon, Saskatchewan, Canada, Feb. 20–21, 1997.

(Continued)

Primary Examiner—Bruce R. Campell
Assistant Examiner—Wendy C Haas
(74) Attorney, Agent, or Firm—David A. Farah; Sheldon & Mak PC

(57) ABSTRACT

The present invention provides an isolated biocontrol agent, or a biocontrol composition, comprising, at least one Pseudomonas strain that exhibits weed suppressive activity. Preferably, the biocontrol composition comprises an acceptable medium such as a liquid culture medium, a solid culture medium, a seed coating, pesta, peat prill, vermiculite, clay, starch, wheat straw, or any combination thereof. The biocontrol agent or biocontrol composition may be used to suppress the growth of a weed. The weed may be selected from the group consisting of green foxtail (*Setaria viridis* [L.] Beauv.), foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), and wild oat (*Avena fatua*). Furthermore, the biocontrol agent or composition may be applied to soil before, during or after planting crops in the soil.

20 Claims, 11 Drawing Sheets

U.S. PATENT DOCUMENTS

| | | | |
|---|---|---|---|
| 5,077,045 A | | 12/1991 | Roberts .................. 424/93 |
| 5,163,991 A | * | 11/1992 | Kennedy et al. ............ 504/117 |
| 5,192,541 A | | 3/1993 | Savage et al. ................ 424/93 |
| 5,332,573 A | | 7/1994 | Yamaguchi et al. ........ 504/117 |
| 5,332,673 A | | 7/1994 | Harris et al. ............. 435/253.3 |
| 5,358,863 A | | 10/1994 | Quimby, Jr. et al. ........ 435/178 |
| 5,472,690 A | | 12/1995 | Winder ...................... 424/93.5 |
| 5,498,591 A | | 3/1996 | Gohbara et al. ............ 504/117 |
| 5,635,444 A | | 6/1997 | Walker et al. .............. 504/117 |
| 5,747,029 A | | 5/1998 | Walker et al. ............. 424/93.5 |
| 5,935,571 A | * | 8/1999 | Aino et al. .............. 424/93.47 |
| 5,952,264 A | | 9/1999 | Walker et al. .............. 504/117 |
| 5,955,348 A | | 9/1999 | Ligon et al. ........... 435/252.34 |
| 5,993,802 A | | 11/1999 | Mallett ...................... 424/93.5 |
| 6,022,828 A | | 2/2000 | Detweiler et al. .......... 504/117 |

OTHER PUBLICATIONS

Boyetchko, S. M. and Mortensen, K., "Uses of Rhizobacteria as Biological Control Agents of Downy Brome," p. 443–448, In: Proceedings of the Soil and Crops Workshop, Saskatoon, Saskatchewan, Canada, Feb. 25–26, 1993.

Connick, Jr., W. J. et al., "Preparation of Stable, Granular Formulations Containing Fusarium *oxysporum* Pathogenic to Narcotic Plants," Biol. Control, 1998, 13: 79–84.

Connick, Jr., W. J., et al., "Formulation of Mycoherbicides Using a Pasta–like Process," Biol. Control 1991, 1: 281–287.

Connick, Jr., W. J. et al., "Shelf life of a bioherbicide product," Am. Biotechnol. Lab. 1996, 14: 34–37.

Connick, Jr., W. J. et al., "Water Activity and Other Factors that Affect the Viability of *Colletotrichum trunactum* Conidia in Wheat Flour–Kaolin Granules ('Pesta')," Biocontrol Sci. Technol. 1996, 6, 277–284.

Daigle, D. J., et al., "Twin–screw extrusion of 'Pesta'–encapsulated biocontrol agents," World J Microbiol. Biotechnol., 1997, 13: 671–676.

Fravel, D. R., et al., "In: Formulation of Microbial Pesticides," p. 187–202, H.D. Burges (Ed.), Kluwer Academic Publishers, Dordrecht, The Netherlands, 1998.

Fundamentals of Fermentation. Techniques for Benchtop Fermentors, 1996; Technical Paper, R & D Lab, New Brunswick Scientific Co., Inc., NJ, USA.

Hall, B. M., et al., "Transport and Survival of alginate–encapsulated and free *lux–lac* marked *Pseudomonas aeruginosa* UG2Lr cells in soil," FEMS Microbiol. Ecol., 1998, 26: 51–61.

Kennedy, A. C., et al., "Rhizobacteria Suppressive to the Weed Downy Brome," Soil. Sci. Soc. AM. J., 1991, 55: 722–727.

Kremer, R., J., et al., "Characterization of Rhizobacteria Associated with Weed Seedings," Appl. Environ. Microbiol., Jun. 1990, p. 1649–1655.

Kremer, R. J., "Bacteria can battle weed growth," Am. Nurseryman, 1986, 164: 162–163.

Leslie, S. B., et al., "Trehalose and Sucrose Protect Both Membranes and Proteins in Intact Bacteria during Drying," Appl. Environ. Microbiol., Oct. 1995, 61: 3592–3597.

Mooney, H.D., et al., "Development of application techniques for biological weed control using rhizobacteria," Proceedings of the IX International Symposium on Biological Control of Weeds, Stellenbosch, South Africa, 1996, p. 297–299.

Mooney, H., Screening and Developmnet of Application Techniques for Rhizobacteria as Biological Control Agents for Green Foxtail (*Setaria viridis* (L.) Beauv.), Thesis, Dept. of Biol. Sci., Simon Fraser Unviversity 1996, pp. 1–89.

Quimby, P.C., et al., "A Simple Method for Stabilizing and Granulating Fungi," Biocontrol Sci. Technol. (1999) 9: 5–8.

Souissi, T., et al., "Leafy Spurge (*Euphorbia esula*) Cell Cultures for Screening Deleterious Rhizobacteria," Weed Science, 1994, 42: 310–315.

* cited by examiner

PRE-EMERGENT BIOLOGICAL CONTROL AGENTS

CROSS-REFERENCE TO RELATED APPLICATION

The present Application claims the benefit of U.S. Provisional Patent Application 60/276,413 titled "Pre-Emergent Biological Control Agents," filed Mar. 16, 2001, the contents of which are incorporated in this disclosure by reference in its entirety.

BACKGROUND

The invention relates to biocontrol agents for suppressing weed growth. More specifically the present invention relates to bacterial biocontrol agents for suppression of weed growth.

Control of weeds is an important aspect of crop management. Due to several undesirable properties associated with the use of chemical herbicides, alternative weed control practices, including the use of biological herbicides, are desired. For example, rising economic, environmental and social costs associated with agricultural inputs, spray drift, pesticide residues, government legislation for reduced pesticide use, along with the development of herbicide resistance in weeds, make biocontrol agents attractive strategies for weed control.

Biological control of weeds with microorganisms (bioherbicides), preferably involves the production and application of a weed-specific pathogen to a target weed. The weed specific pathogen is typically a fungus or bacterial pathogen that inhibits or suppresses root, shoot or both root and shoot growth, development, or both growth and development, thereby reducing weed competition. The development of biological crop protection products (bioherbicides) for economically important weed problems in agricultural field crops may help to facilitate harvests, secure yields, and protect the environment. Biological control provides an additional tool to complement an integrated weed management system and helps sustainable agricultural systems by maintaining the ecosystem balance through the preservation of plant and microbial diversity in the field.

An important aspect in the development of a successful biological control agent is an effective delivery system which can be readily integrated into existing farming practices and commercial production. Rhizobacteria (root-colonizing bacteria) being developed as bioherbicides have been encapsulated into sodium alginate granules and shown to be a suitable method for survival and distribution of microbial inocula in the soil environment (Hall, B. M., A. J. McLoughlin, K. T. Leung, J. T. Trevors and H. Lee 1998. Transport and survival of alginate-encapsulated and free lux-lac marked *Pseudomonas aeruginosa* UG2Lr cells in soil. FEMS Microbiol. Ecol. 26:51–61.; and Mooney, H. D., S. M. Boyetchko, and Z. K. Punja. 1996. Development of application techniques for biological weed control using rhizobacteria. p. 297–299 in IX International Symposium on Biological Control of Weeds, Stellenbosch, South Africa.). Another method of encapsulation is the 'Pesta' process (Connick, W. J. Jr., C. D. Boyette and J. R. McAlpine 1991. Formulation of mycoherbicides using a pasta-like process. Biol Control 1:281–287.), which has been shown to extend the shelf-life of a dried encapsulated bioherbicide (Connick, W. J. Jr., D. Daigle, K. Williams, B. Vinyard, D. Boyette and P. J. Quimby Jr. 1996. Shelf life of a bioherbicide product. Am. Biotechnol. Lab. 14:34–37.; Connick, W. J. Jr., D. J. Daigle, C. D. Boyette, K. S. Williams, B. T. Vinyard and P. C. Quimby Jr. 1996. Water activity and other factors that affect the viability of *Colletotrichum truncatum* conidia in wheat flour-kaolin granules ('Pesta). Biocontrol Sci. Technol. 6:277–284.; and Connick, W. J. Jr., D. J. Daigle, A. B. Pepperman K. P. Hebbar, R. D. Lumsden, T. W. Anderson and D. C. Sands 1998. Preparation of stable, granular formulations containing *Fusarium oxysporum* pathogenic to narcotic plants. Biol Control 13:79–84.).

There are several documents disclosing the use of fungi as biocontrol agents. For example, U.S. Pat. No. 5,993,802 teaches methods for suppressing the growth of *Calamagrostis canadensis* using an isolate of a low temperature basidiomycete fungus, *Coprinus psychromorbidus*. U.S. Pat. No. 5,472,690 teaches of a mycoherbicide (including at least one or both of *Fusarium nivalis* and *Colletotrichum calamagrostidis*) effective in the control of *Calamagrostis canadensis* and/or related grasses. The control of crabgrass using fungi is disclosed in U.S. Pat. No. 5,952,264, using the fungus *Cochliobolus intermedius*, and U.S. Pat. No. 5,635,444 using a fungus selected from the genus Curvularia. U.S. Pat. No. 5,747,029, teaches the control of sicklepod weeds using the fungus *Myrothecium verrucaria*. The control of nutsedge weeds using the fungus *Dactylaria higginsii* is disclosed in WO 98/08389. U.S. Pat. No. 4,606,751 teaches the biocontrol of Johnson grass using *Bipolaris sorghicola* spores that are suspended in a solution of water and surfactant, and sprayed onto a field in which the weed is growing.

U.S. Pat. No. 6,022,828 discloses the use of a *Xanthomonas campestris* pathovar (a bacteria) as a bioherbicide for controlling *Poa trivialis*. Strains of *Drechslera monoceras* which show herbicidal effects against all varieties of barnyard grass, for example Echinochloa spp is taught in U.S. Pat. No. 5,498,591. Modified and unmodified soil and rhizoplane bacterial strains, specifically *Pseudomonas putida* strain (FH160), useful for the control of weeds such as downy brome, Japanese brome and jointed goatgrass in the vicinity of wheat is presented in U.S. Pat. No. 5,332,673. U.S. Pat. No. 5,332,573 discloses the use of strains of Drechslera which possess herbicidal effects against all varieties of barnyard grass such as Echinochloa. U.S. Pat. Nos. 5,192,541 and 5,077,045 both teach the control of weed grasses by infecting them with a *Xanthomonas campestris* pathovar. U.S. Pat. No. 5,030,562 discloses the use of non-fluorescent Pseudomonas strains which inhibit downy brome. Japanese Patent 10179139 teaches *Drechslera monoceras* having selected herbicidal activities against Echinochloa. European Patent EP 839,449 discloses a herbicide containing phytopathogenic microorganisms such as Drechslera or Exserohilum.

The combination treatment of applying a chemical such as a herbicide (glyphosate) and a bacterial plant pathogen (*Pseudomonas synringae* pv. tabaci) for controlling the growth of weeds is disclosed in WO 91/03161. The use of genetically modified Pseudomonas strains that have enhanced biocontrol properties against fungi such as Rhizoctonia and Pythium is taught in U.S. Pat. No. 5,955,348.

Annual grassy weeds such as *Setaria viridis* (L.) Beauv. (commonly known as green foxtail, pigeongrass, wild millet, green bristlegrass, and bottlegrass) and *Avena fatua* (L.) (commonly known as wild oat) develop dense competitive stands and have heavy seed production in spring sown crops. Green foxtail is a principal weed of corn, soybean, cereals, flax, canola, sugar beets, and pastures. Wild oat is considered to be one of the three most serious weed problems in cereal production areas. The amount of damage to the crop depends on the density of the stand, time of emergence, and length of time the weed and crop are competing. Weed surveys for herbicide-resistant wild oat and green foxtail have revealed that there is a high incidence of group-1 herbicide-resistant wild oat populations (48% of fields surveyed) and 28% had either group-1 or group-3 herbicide-resistant green foxtail populations (Beckie, H. J., A. Legere, A. G. Thomas, L. T. Juras, and M. D. Devine. 1996 Survey of Herbicide-Resistant Wild Oat and Green Foxtail in Saskatchewan: Interim Report. AAFC Report, 22 pp.). Therefore, biocontrol of these and other plants, for example, foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), green foxtail (*Setaria viridis*), and wild oat (*Avena fatua*) is highly desirable. However, for most of these weeds there are no known biocontrol agents.

SUMMARY

The invention relates to biocontrol agents for suppressing weed growth. More specifically the present invention relates to bacterial biocontrol agents for suppression of weed growth.

The present invention provides an isolated biocontrol agent comprising at least one Pseudomonas strain that exhibits weed suppressive activity. Preferably, the biocontrol agent is selected from the group consisting of bacterial strains BRG100, BRG168, BRG3, BRG10, BRG12, BRG16, BRG21, BRG22, BRG24, BRG64, BRG80, OY4GFT9, and bacterial strain 189.

According to another aspect of the present invention, there is provided a biocontrol agent selected from the group consisting of bacterial strain BRG100 (IDAC 141200-1), bacterial strain 189 (IDAC 141200-3), bacterial strain BRG168 (IDAC 141200-2), and OY4GFT9 (IDAC 141200-5).

The present invention is also directed to a biocontrol composition comprising, at least one Pseudomonas strain that exhibits weed suppressive activity, in an acceptable medium. Preferably, the at least one Pseudomonas strain within the biocontrol composition is selected from the group consisting of bacterial strains BRG100, BRG168, BRG3, BRG10, BRG12, BRG16, BRG21, BRG22, BRG24, BRG64, BRG80, 189 and OY4GFT9. Furthermore, it is preferred that the acceptable medium of the biocontrol composition comprise a liquid culture medium, a solid culture medium, a seed coating, pesta, peat prill, vermiculite, clay, starch, wheat straw, or any combination thereof.

According to another aspect of the present invention, there is provided the use of a biocontrol agent comprising at least one Pseudomonas strain that exhibits weed suppressive activity for the suppression of growth of weeds.

According to a further aspect of an embodiment of the present invention there is provided a biocontrol composition comprising at least one biocontrol agent selected from the group consisting of bacterial strain BRG100 (IDAC 141200-1), bacterial strain 189 (IDAC 141200-3), bacterial strain BRG168 (IDAC 141200-2), and bacterial strain OY4GFT9 (IDAC 141200-5) formulated in an acceptable medium. The medium may comprise liquid culture medium, semi-solid culture medium or solid culture medium such as minimal medium, nutrient broth, M9 media, pesta, peat prills, vermiculite, clay, starches, wheat, straw, or any combination thereof.

According to a further aspect of an embodiment of the present invention there is provided a method of suppressing weeds during crop growth comprising; adding an effective amount of a biocontrol composition comprising at least one bacterial strain selected from the group consisting of BRG100 (IDAC 141200-1), bacterial strain 189 (IDAC 141200-3), BRG168 (IDAC 141200-2), and OY4GFT9 (IDAC 141200-5) formulated in an acceptable medium to soil, planting crops in the soil comprising the biocontrol composition and growing the crops.

FIGURES

These and other features, aspects and advantages of the present invention will become better understood with regard to the following description, appended claims, and accompanying figures where:

Figure 4A:
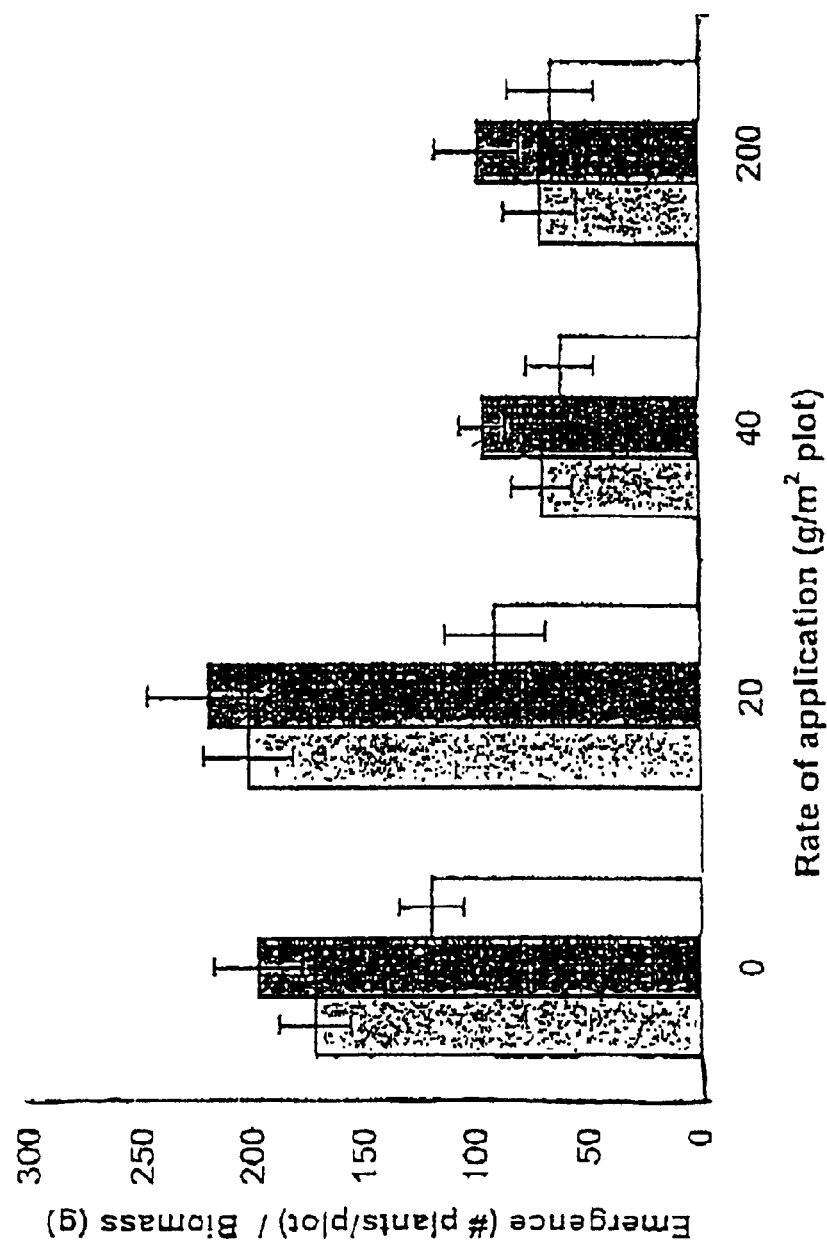
Figure 4B:
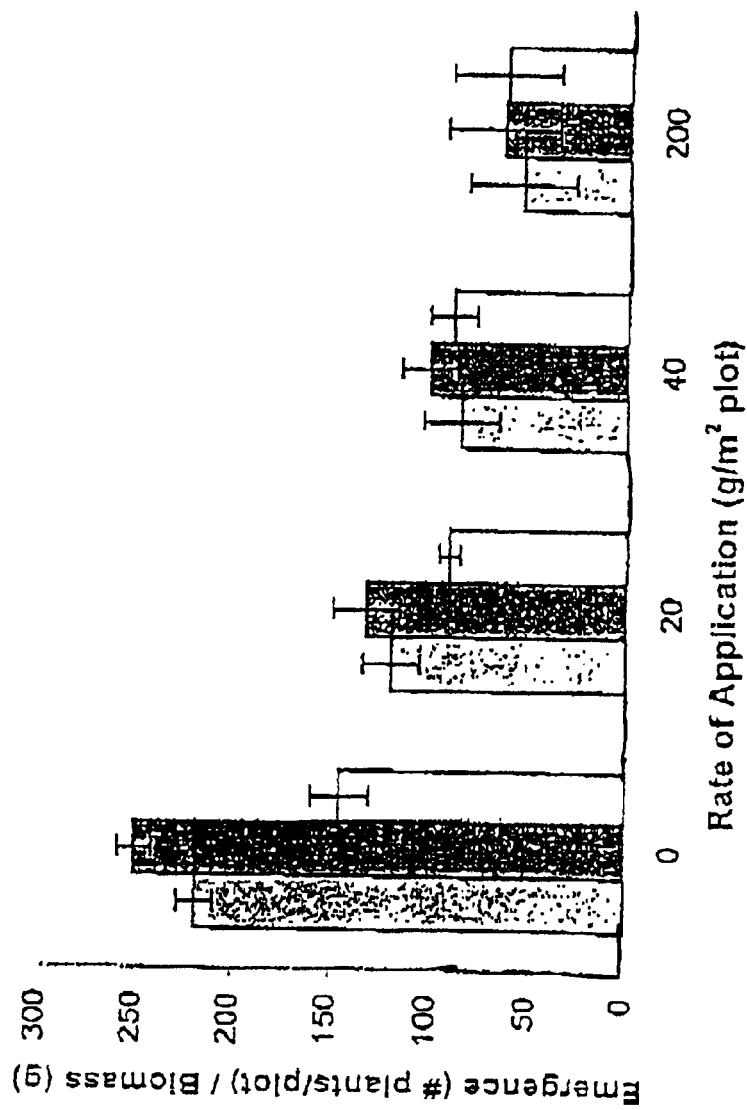
Figure 4C:
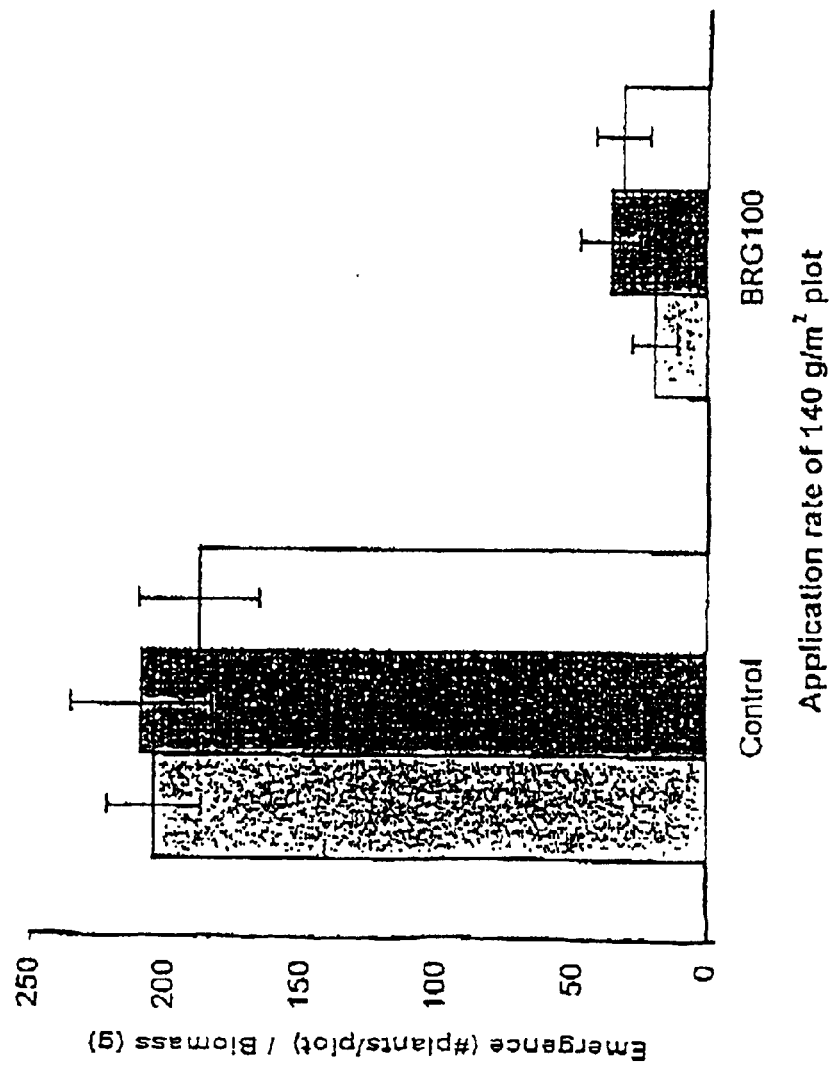
Figure 5A:
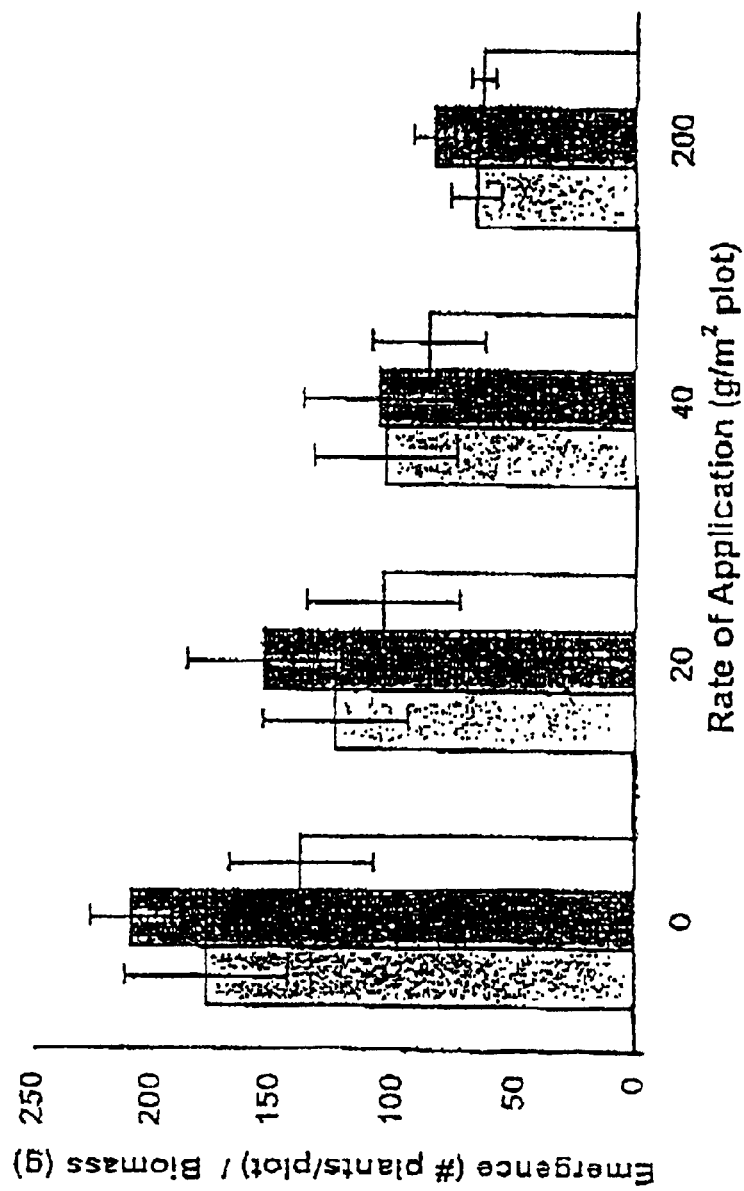
Figure 5B:
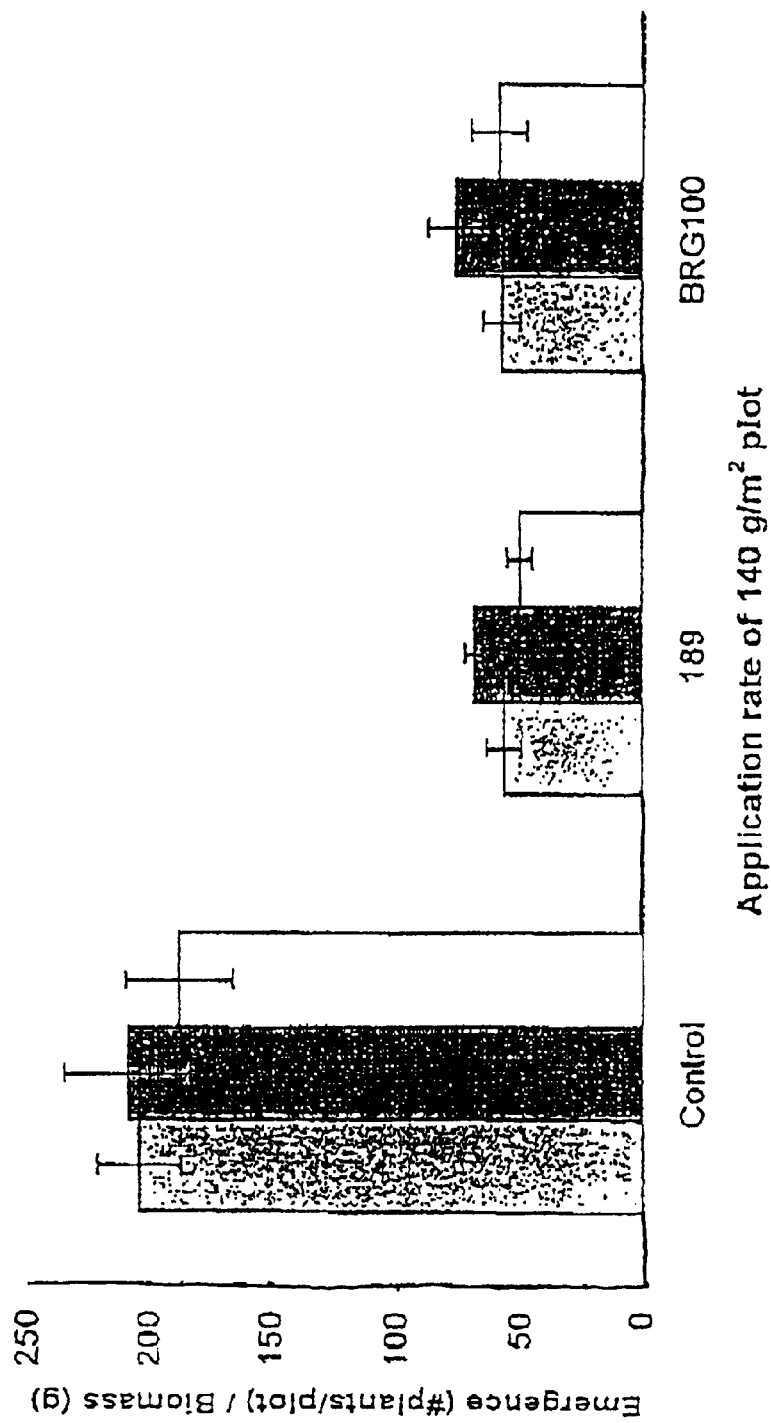
Figure 6A:
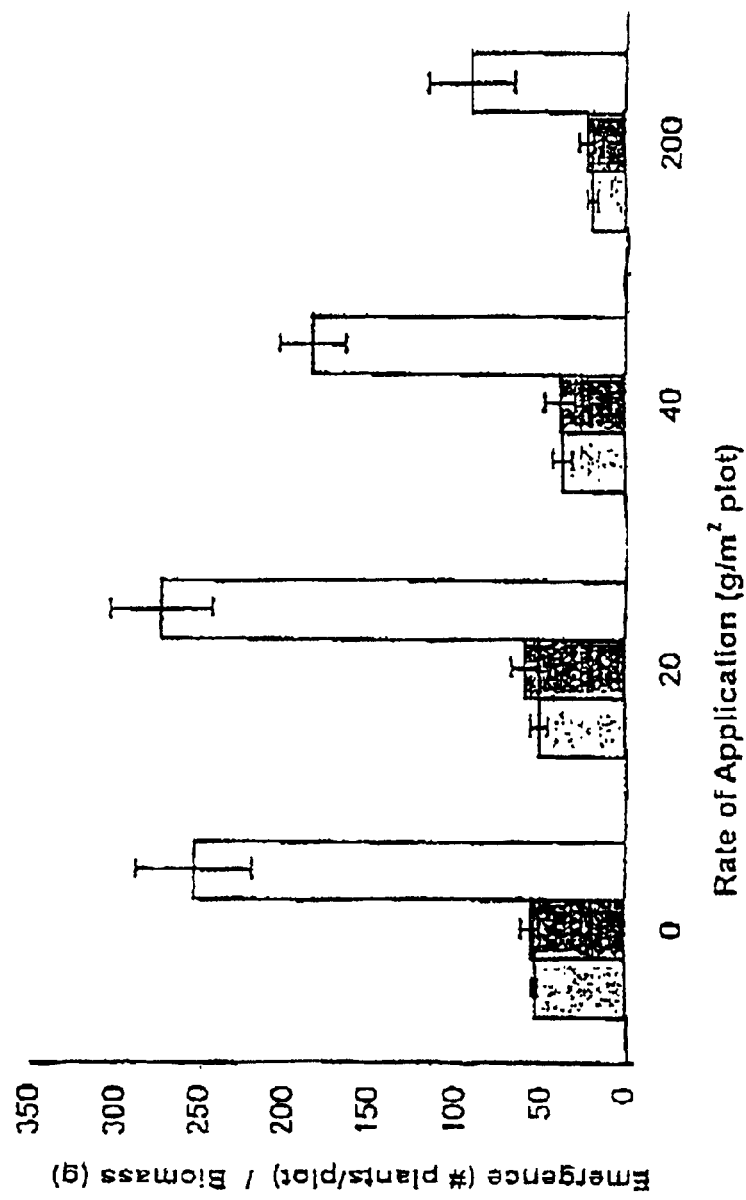
Figure 6B:
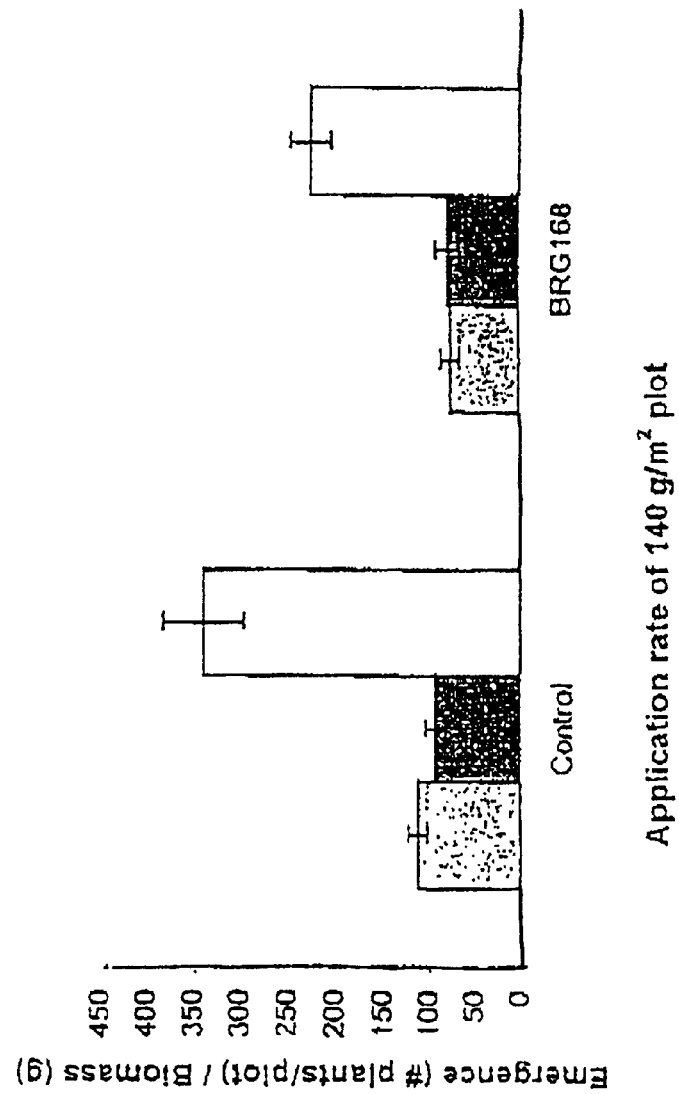
Figure 7:
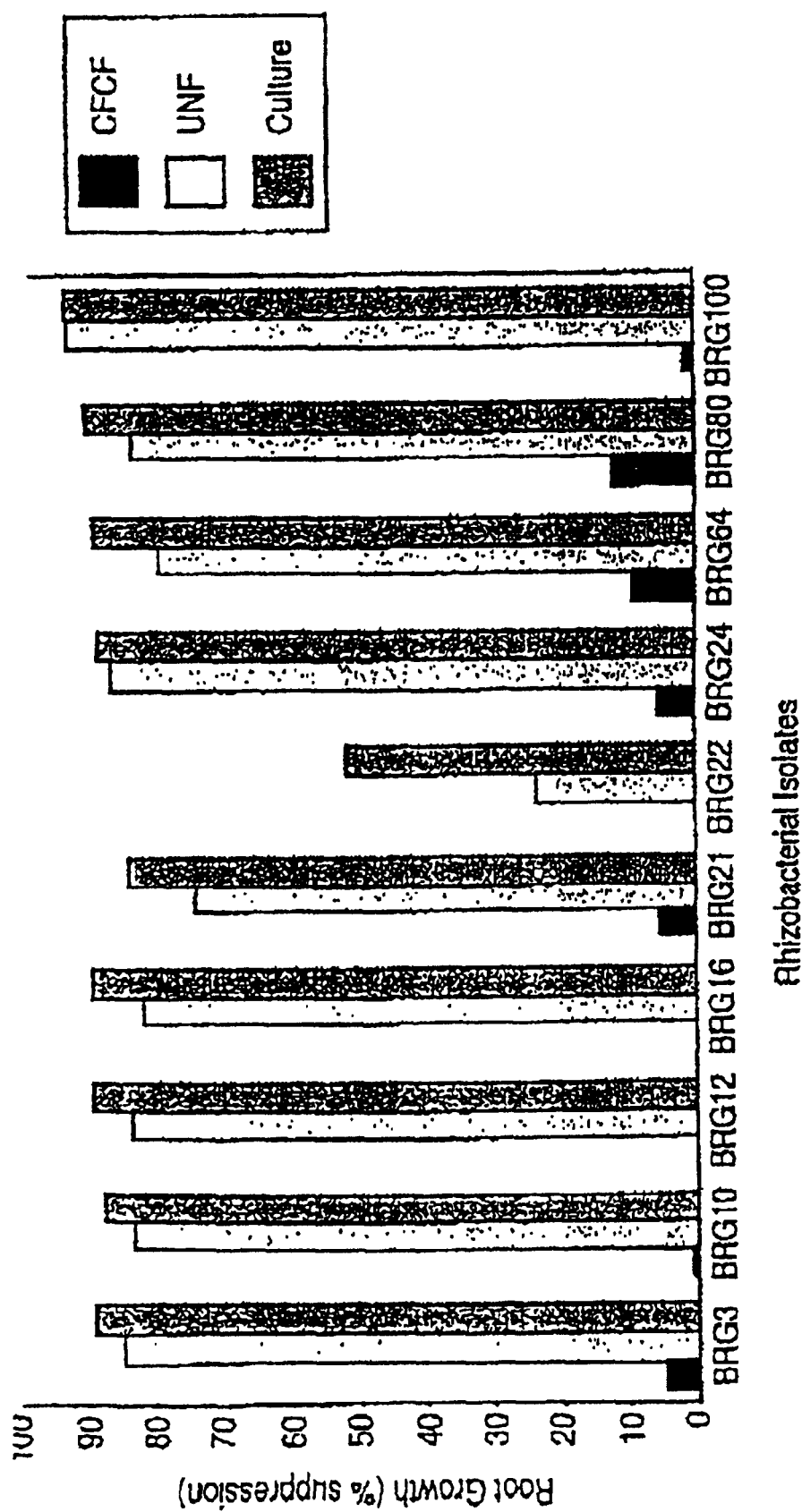

FIG. 4 shows the effect of BRG100 in a range of different formulations on suppressing emergence of green foxtail in field trials. FIG. 4(A) shows the effect of increasing BRG100 concentration in peat prill formulation on emergence (determined as number of plants per plot) at 4 weeks (grey bar), 8 weeks (black bar), and on plant biomass (open bar). FIG. 4(B) shows the effect of increasing BRG100 concentration in pesta formulation on emergence (determined as number of plants per plot) at 4 weeks (grey bar), 8 weeks (black bar), and on plant biomass (open bar). FIG. 4(C) shows the effect of BRG100 in pesta formulation, applied at a rate of about 140 g/m$^2$, compared with control treatment, on emergence (determined as number of plants per plot) at 4 weeks (grey bar), 8 weeks (black bar), and on plant biomass (open bar);

FIG. 5 shows the effect of bacterial strain 189 in a range of different formulations on suppressing emergence of green foxtail in field trials, where FIG. 5(A) shows the effect of increasing bacterial strain 189 concentration in peat prill formulation on emergence (determined as number of plants per plot) at 4 weeks (grey bar), 8 weeks (black bar), and on plant biomass (open bar), and FIG. 5(B) shows the effect of bacterial strain 189 and BRG100 in peat prill formulation, applied at a rate of about 140 g/m$^2$, compared with control treatment, on emergence (determined as number of plants per plot) at 4 weeks (grey bar), 8 weeks (black bar), and on plant biomass (open bar);

FIG. 6 shows the effect of bacterial strain BRG168 in peat prill formulation on suppressing emergence of wild oat in field trials, and FIG. 6(A) shows the effect of increasing bacterial strain BRG168 concentration on emergence (determined as number of plants per plot) at 4 weeks (grey bar), 8 weeks (black bar), and on plant biomass (open bar), and FIG. 6(B) shows the effect of BRG168 applied at a rate of about 140 g/m$^2$, compared with control treatment, on emergence (determined as number of plants per plot) at 4 weeks (grey bar), 8 weeks (black bar), and on plant biomass (open bar); and FIG. 7 shows the suppression of green foxtail root growth by a range of Pseudomonas spp. isolates, in either cell-free culture filtrate (solid bar), unfiltered centrifuged supernatant (light grey bar) and whole bacterial culture (dark grey bar).

DESCRIPTION

The invention relates to biocontrol agents for suppressing weed growth. More specifically the present invention relates to bacterial biocontrol agents for suppression of weed growth. The following description is of a preferred embodiment by way of example only and without limitation to the combination of features necessary for carrying the invention into effect.

All reference cited in this disclosure are incorporated by reference in their entirety.

As used in this disclosure, the term "biocontrol agent" means a microorganism which suppresses the growth of, or kills, a target pest, for example, but not limited to a plant or a weed. More specifically, the biocontrol agents of the present invention may be used to suppress the growth of one or more target pests. Without wishing to be bound by theory, the biocontrol agent suppresses the growth of a target pest, for example, a plant or weed (i.e., exhibits weed suppressive activity), by interfering with the normal growth and development of the target plant or weed. For example, but not wishing to be limiting, the biocontrol agent may inhibit root growth, shoot growth, reduce biomass, inhibit seed production, reduce competitiveness of the target plant or weed for a crop's water and nutrients, or a combination thereof. Preferably, the biocontrol agent is a bacterial biocontrol agent obtained from Pseudomonas, for example either *Pseudomonas fluorescens*, or *Pseudomonas aureofaciens*. More preferably, the biocontrol agent is selected from the group consisting of:

BRG100 (*Pseudomonas fluorescens* biovar C or G, deposited Dec. 14, 2000, International Depository Authority of Canada (IDAC), National Microbiology Laboratory, Health Canada, 1015 Arlington St., Winnipeg, Manitoba, R3E 3R2 as IDAC 141200-1);

BRG168 (*Pseudomonas fluorescens* biovar B or F; deposited Dec. 14, 2000, IDAC 141200-2);

189 (*Pseudomonas aureofaciens*; deposited Dec. 14, 2000, IDAC 141200-3);

OY4GFT9 (*Psuedomonas putida*, biovar D, deposited Dec. 14, 2000, IDAC 141200-5); and a combination thereof. However, as described below (also see FIG. 7), other Pseudomonas isolates also exhibit weed suppressive activity and may be used as a biocontrol agent, and therefore, the present invention is not to be considered as being limited to BRG100, BRG168, OY4GFT9, or bacterial strain 189.

As will be understood by those with skill in the art with reference to this disclosure, in order for the bacterial strains of the present invention to be grown, cultured or used in accordance with the embodiments of the present invention, it is preferable that the bacterial strains be grown in a suitable medium to produce a biocontrol composition or formulation. By the term "suitable medium" or "acceptable medium" it is meant any liquid, semi-liquid or solid substrate which allows a bacterial strain to grow, or to remain viable, or both grow and remain viable, for example during storage. Furthermore, the bacterial strain may be formulated as indicated below prior to use. Such formulations are also considered suitable or acceptable media in the context of the present invention. Preferably, the formulation permits an effective amount of one or more bacterial strains to remain viable prior to, and after, being applied to a crop. More preferably, the medium, formulation, or both medium and formulation permits one or more bacterial strains to remain viable after about 1 to about 3 months following application of the bacteria to the soil.

The present invention also contemplates producing the bacterial strains in various types of media, for example, but not wishing to be limiting minimal liquid culture medium (Example 1), nutrient broth, M9 media and REC media, and formulations in pesta, peat prills, vermiculite, clay, starches, wheat straw (see for example Connick et al. 1991; Fravel, D. R., W. J. Connick, Jr., and J. A. Lewis, 1998. Formulation of microorganisms to control plant diseases. p. 187–202 In: H. D. Burges (Ed.), Formulation of Microbial Biopesticides, Kluwer Academic Publishers, Dordrecht, The Netherlands.; Quimby, P. C. Jr., N. K. Zidack, C. D. Boyette and W. E. Grey 1999. A simple method for stabilizing and granulating fungi. Biocontrol Science and Technology 9:5–8.; U.S. Pat. Nos. 5,074,902; 5,358,863; and International Publication WO 98/05213, or any combination or variant thereof, provided that the formulation allows the bacterial strain to remain viable. The biocontrol agent may also be applied to the surface of the seed in a suitable formulation or composition as would be known to one of skill in the art. Furthermore, it is contemplated that the bacterial strains, in a suitable formulation, may be applied before, during or after seeding a crop.

Pesta is a term for a granular product made from a cereal grain flour and a biocontrol agent. The process encapsulates biocontrol agents in pasta-like products called pesta (U.S. Pat. No. 5,074,902; and Connick et al. 1991). Bacteria formulated in such media may exhibit extended shelf and field-life (e.g. Connick, W. J. Jr., D. Daigle, K. Williams, B. Vinyard, D. Boyette and P. J. Quimby Jr. 1996. Shelf life of a bioherbicide product. Am. Biotechnol. Lab. 14:34–37.; and Connick et al. 1998). These characteristics are desired in a product which may be stored prior to use or shipped over long-distances prior to being used for weed control in a field. Therefore, the biocontrol compositions of the present invention may be formulated in a suitable composition, for example, but not limited to, pesta.

As described in more detail below, the present invention provides one or more biocontrol agents that may be used for suppressing the growth of a plant, for example but not limited to, foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), green foxtail (*Setaria viridis*), and wild oat (*Avena fatua*). Preferably, the biocontrol agents suitable for suppressing the growth of weed species is BRG100 (IDAC 141002-1), alone or in combination with BRG168 (IDAC 141200-2), 189 (IDAC 141200-3) or both BRG168 and 189. However, other Pseudomonas spp. may also be effectively used as described herein. For example, which is not to be considered limiting in any manner, a biocontrol agent to control the growth of green foxtail, crabgrass, annual rye grass, barnyard grass, yellow foxtail, Italian rye grass, and other weeds, may be selected from the group consisting of bacterial strain BRG100, bacterial strain 189, or a combination of strain BRG100, strain 189. A biocontrol agent that may be used for the suppression of growth of wild oat, yellow foxtail, green foxtail, crabgrass, barnyard grass, goose grass and other weeds, is bacterial strain BRG168. Furthermore, bacterial strain OY4GFT9 (IDAC 141200-5) may be used to control the growth of crabgrass, annual rye grass, barnyard grass, green foxtail and Goose grass.

Therefore, according to an aspect of an embodiment of the present invention, there is provided the use of a biocontrol agent consisting of bacterial strain BRG100, bacterial strain 189, and bacterial strain BRG168, or a combination thereof for the suppression of weeds. In an aspect of a preferred embodiment, the present invention contemplates the use of the biocontrol agent consisting of bacterial strain BRG100, bacterial strain 189, or a combination thereof for suppression of foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiforum*), Goose grass (*Eleusine indica*), *Setaria viridis*, and wild oat (*Avena fauta*).

In a further aspect of an embodiment of the present invention there is provided a biocontrol composition comprising a biocontrol agent selected from the group consisting of bacterial strain BRG100, bacterial strain 189, bacterial strain OY4GFT9, and bacterial strain BRG168, in a suitable medium or formulation.

The efficacy of the bacterial strains of the present invention for weed suppression may be monitored using any means known within the art, for example, but not limited to, a growth pouch bioassay (see Example 3). Such an assay compares root and shoot growth in the presence and absence of the bacterial strain. As demonstrated in Example 3, the biocontrol agents of the present invention may be used to suppress the growth of a variety of weed plants, for example, but not limited to foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), green foxtail (*Setaria viridis*), and wild oat (*Avena fauta*).

Figure 1:
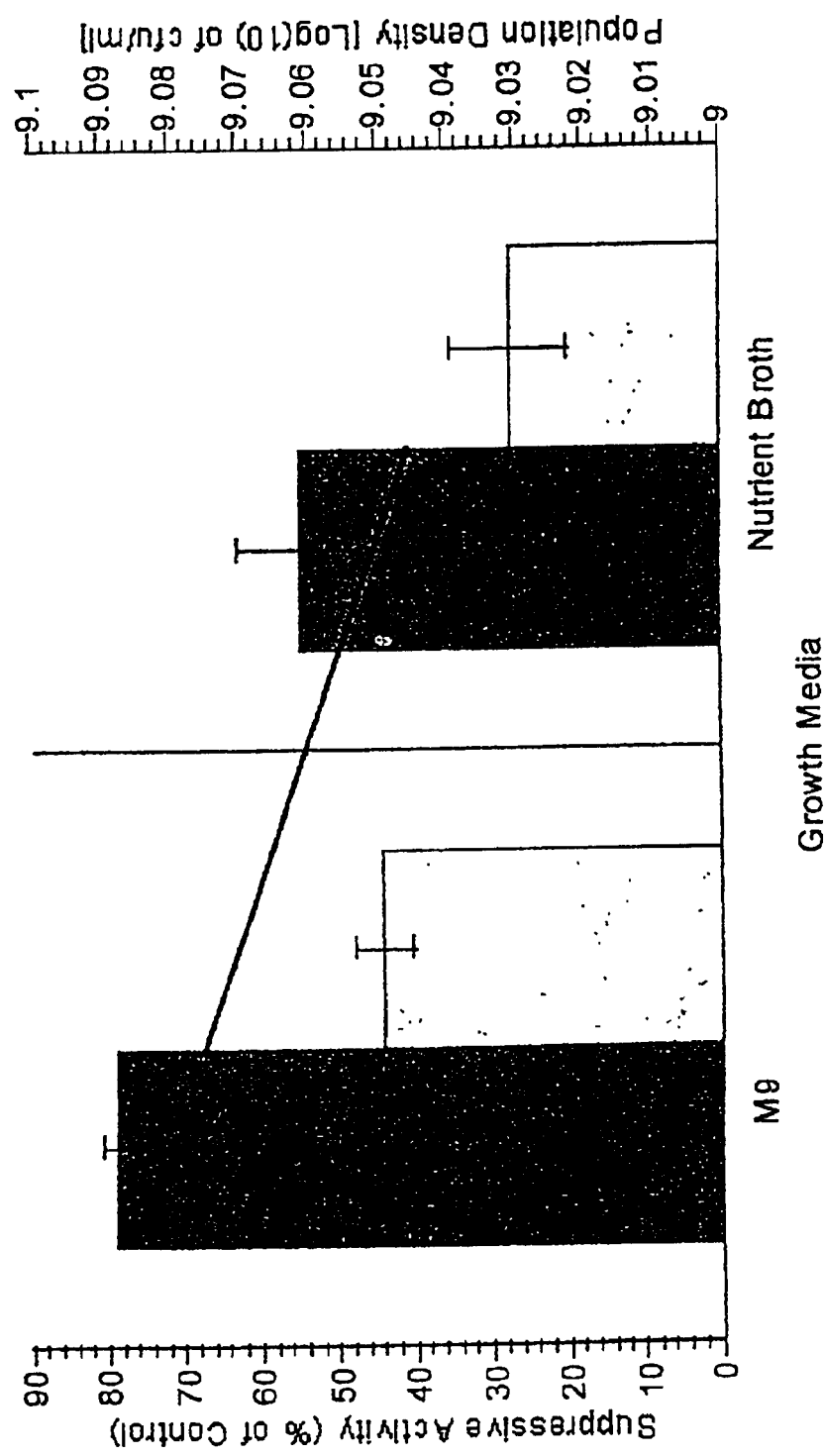
FIG. 1 shows the suppression of root (solid bar) and shoot (open bar) growth of green foxtail by BRG100, and bacterial density (solid line), using either M9 or nutrient broth media, as determined using growth pouch bioassays.

The suppression of root and shoot growth of green foxtail by BRG100 in M9 medium and a nutrient broth medium is shown in FIG. 1. The nutrient broth allows for the growth of bacterial strain BRG100 and suppresses root and shoot growth of green foxtail by about 50% (root) and about 30% (shoot). In contrast, the M9 medium suppresses root and shoot growth by about 80% and about 40%, respectively. Under equivalent growth conditions, M9 medium allows for slightly increased bacterial growth, with the production of a bacterial population density of about $\log_{10}$ 9.075 versus about 9.045 for the nutrient broth medium.

Figure 2:
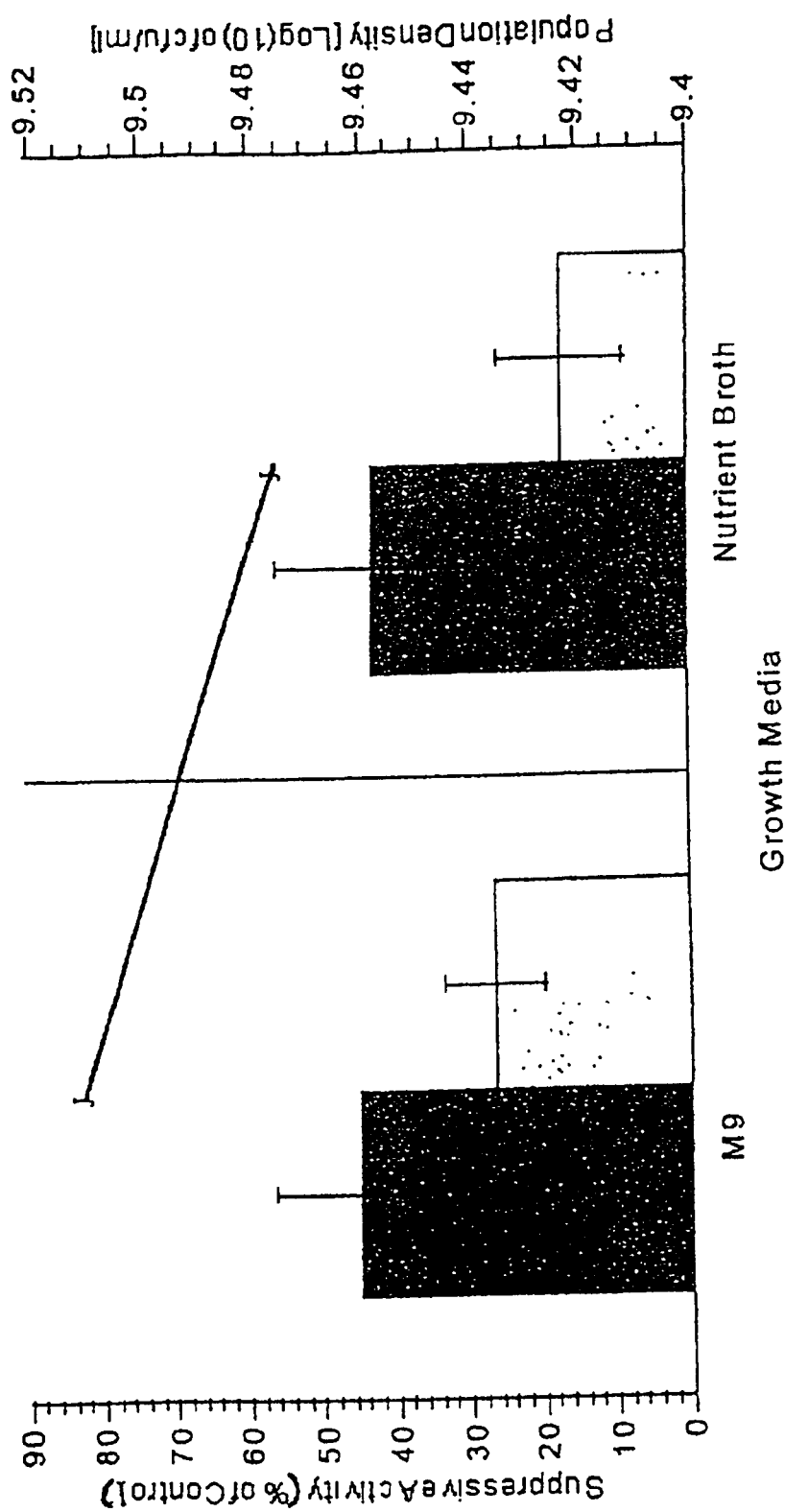
FIG. 2 shows the suppression of root (solid bar) and shoot (open bar) growth of green foxtail by 189, and bacterial density (solid line), using either M9 or nutrient broth media, as determined using growth pouch bioassays.

Referring now to FIG. 2, there is shown the suppression of root and shoot growth by bacterial strain 189 on green foxtail in M9 medium and in nutrient broth medium. As shown in FIG. 2, the nutrient broth allows the growth of bacterial strain 189 and suppresses shoot and root growth by about 40% and about 20%, respectively. In contrast, the M9 medium suppresses root and shoot growth by about 45% and about 25%, respectively. Under equivalent growth and seeding conditions, the M9 medium allows for the production of a bacterial population density of about $\log_{10}$ 9.51 versus about 9.47 for the nutrient broth medium.

Figure 3:
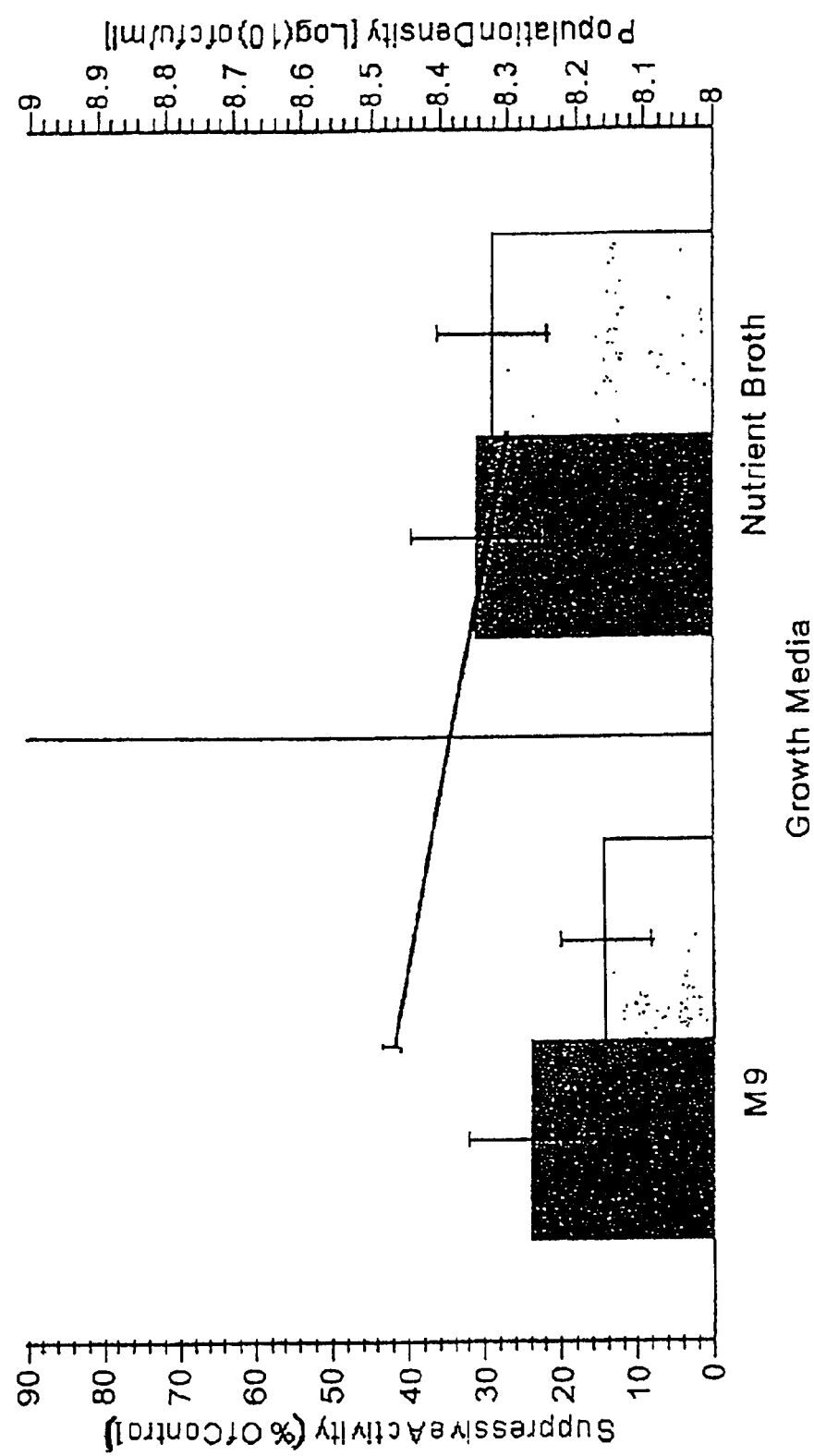
FIG. 3 shows the suppression of root (solid bar) and shoot (open bar) growth of green foxtail by BRG168, and bacterial density (solid line), using either M9 or nutrient broth media, as determined using growth pouch bioassays.

Referring now to FIG. 3, there is shown the suppression of root and shoot growth by BRG168 on wild oat in M9 medium versus nutrient broth medium (see Example 1). The nutrient broth allows the growth of BRG168 and suppresses root and shoot growth by about 30%. M9 medium suppresses root and shoot growth by about 25% and about 15% respectively. However, under equivalent growth and seeding conditions, M9 medium allows the growth of a log bacterial population density of about 8.5 versus about 8.3 for the nutrient broth medium.

Collectively, the results depicted in FIGS. 1, 2 and 3 suggest that the components of a medium may influence the suppression of weeds by bacterial strains. However, a medium which enhances the growth of a biocontrol agent and that allows it to grow to a greater population density may not necessarily exhibit an increase in suppression of weeds, as suggested by FIG. 3.

Comparing the effects of individual carbon sources on root and shoot suppression, it is noted that a medium comprising a carbon source such as, but not limited to mannitol or sucrose exhibit greater suppression of weeds than does a medium comprising a yeast extract or a medium with no carbon source. Combinations of carbon sources results in an increased suppression of root and shoot growth. For example, combining 2 and 3 carbon sources in the same fermentation media increased the ability of BRG168 to suppress root and shoot growth (root and shoot suppression is approximately 20% with carbon sources such as mannitol, trehalose and sucrose). Mannitol may enhance root and shoot suppression by a bacteria. Sucrose and trehalose may enhance the production of bacteria (cfu/ml) when formulated in a medium. Without wishing to be bound by theory, sucrose and trehalose may stabilize cell membranes and thus contribute to enhanced bacterial growth. Thus, the present invention contemplates media comprising one or more carbon sources such as, but not limited to sucrose, trehalose, yeast extract, mannitol or a combination thereof.

The present invention also contemplates compositions of a Pseudomonas strain that exhibits a weed suppressive activity, for example but not limited to, the bacterial strains, BRG100 (IDAC 141200-1), 189 (IDAC 141200-3), BRG168 (IDAC 141200-2) and OY4 GFT9 (IDAC 141200-5) in liquid, semi-solid or solid media, or formulation such as but not limited to pesta, peat prills, vermiculite, clay, starches, wheat straw or any combination thereof.

Referring to FIGS. 4(A)–(C), there is shown the effect of bacterial strain BRG100 on green foxtail weed emergence in the field at 4 and 8 weeks post application and on total weed biomass after 8 weeks. As shown in FIG. 4(A), BRG100 applied as, for example but not limited to, a peat prill formulation suppresses the emergence of green foxtail weed and reduces its biomass. The results demonstrate that bacterial strain BRG100 in a peat prill formulation suppresses the emergence of green foxtail weed and reduces its biomass.

FIG. 4(B) depicts, for example but not limited to, a pesta formulation of BRG100 on the suppression of green foxtail weed emergence and biomass, and demonstrates that various formulations of BRG100 may be used to suppress green foxtail weed emergence and reduce total weed biomass. FIG. 4(C) depicts the efficacy of applying about 140 g/m$^2$ of, for example but not limited to, a pesta-formulated BRG 100 compared to a control treatment. Collectively, FIGS. 4(A)–(C), demonstrate that BRG100, in a variety of formulations, is capable of suppressing green foxtail weed emergence and reducing total weed biomass under varying field conditions.

Therefore, the present invention provides for the use of bacterial strain BRG100 grown and formulated in a suitable composition for the suppression of green foxtail growth. Preferably, the bacteria are applied at an amount of about 1 g/m$^2$ to about 500 g/m$^2$. More preferably, the bacteria are applied at an amount of about 20 g/m$^2$ to about 200 g/m$^2$. However, as someone of skill in the art will understand, the amount of the biocontrol composition required for suppression of green foxtail weeds may be dependent on the medium in which the bacterial strain is formulated and the method in which it is formulated. For example, but not wishing to be limiting, a formulation and medium which permits a greater percentage of bacteria to remain viable may require less biocontrol composition to suppress weeds than does another formulation and medium in which the same strain of bacteria is less viable. Further, the amount of a biocontrol composition required for suppression of weeds may be influenced by environmental factors such as but not limited to temperature, humidity, soil pH, soil type and other factors and will depend on formulation characteristics such as granule size, bio-release capabilities and placement of formulations in relation to standard agronomic principles.

Result from field trails demonstrate that BRG100 is effective in controlling green foxtail under a variety of field conditions including dry growth conditions (see Table 3 and 4, Example 4). Furthermore, at high concentrations, for example but not limited to $10^6$ to about $10^9$ cfu BRG100/gram formulation, weed suppressive activity is observed at low application rates. Examples of low application rates include but are not limited to 1–5 $g/m^2$. The biocontrol agent may also be applied throughout the growing season and still exhibit weed suppressive activity (see Table 4, and supporting text).

Referring to FIGS. 5(A) and 5(B), there is shown the effect of bacterial strain 189 on green foxtail weed emergence in the field at 4 and 8 weeks post application and on total weed biomass after 8 weeks post application. FIG. 5(A), shows that bacterial strain 189 applied as, for example but not limited to, a peat prill formulation suppresses the emergence of green foxtail weed and reduces its biomass. The results demonstrate that bacterial strain 189 formulated in a peat prill medium suppresses the emergence of green foxtail weeds and reduces its biomass.

FIG. 5(B) compares the efficacy of bacterial strain 189 against that of BRG100 for suppression of green foxtail weed emergence and biomass following an application of 140 $g/m^2$ of the respective bacteria in, for example but not limited to, a peat prill biocontrol composition. The results indicate that bacterial strain 189 and BRG100 are similar in their abilities to suppress green foxtail weed emergence and biomass.

Therefore, the present invention provides for the use of bacterial strain 189 formulated in a suitable medium for the suppression of green foxtail growth.

Result from field trails demonstrate that bacterial strain 189 is effective in controlling green foxtail under a variety of field conditions including dry growth conditions (see Table 5, Example 4). Furthermore, at high concentrations, for example but not limited to $10^6$ to about $10^9$ cfu 189/gram formulation, weed suppressive activity is observed at low application rates. Examples of low application rates include but are not limited to 1–5 $g/m^2$. The biocontrol agent may also be applied throughout the growing season and still exhibit weed suppressive activity (see Table 5, and supporting text).

Referring to FIGS. 6(A) and (B), there is shown the effect of bacterial strain BRG168 on wild oat weed emergence at 4 and 8 weeks post application and on total weed biomass at 8 weeks post application. FIG. 6(A), indicates that, for example but not limited to, a peat prill biocontrol composition of BRG168 suppresses the emergence, and reduces the biomass, of wild oat weed. FIG. 6(B) depicts the suppression of wild oat weeds following an application of BRG168 formulated in, for example but not limited to, peat prills and applied at about 140 $g/m^2$ at a second site from the location where the results for FIG. 6(A) was obtained. FIG. 6(B) demonstrates that bacterial strain BRG168 is capable of suppressing wild oat weed emergence and biomass, and collectively, FIGS. 6(A) and 6(B) demonstrate that bacterial strain BRG168 is effective under varying field conditions.

Further screening of Pseudomonas spp. strains indicates that many other biovars are also active in suppressing weed growth. For example, FIG. 7 demonstrates that BRG3, BRG10, BRG12, BRG16, BRG21, BRG22, BRG24, BRG64, BRG80 and BRG100 are each effective in suppressing root growth. Therefore, the present invention pertains to a *Pseudomonas fluorescens*, or a *Pseudomonas aureofaciens* biovar that exhibits a weed suppressive activity and suppresses weed growth.

The above description is not intended to limit the claimed invention in any manner, furthermore, the discussed combination of features might not be absolutely necessary for the inventive solution.

The present invention will be further illustrated in the following examples. However, it is to be understood that these examples are for illustrative purposes only, and should not be used to limit the scope of the present invention in any manner.

EXAMPLE 1

Liquid Media, Fermentation Media and Buffer Formulations

1. Nutrient Broth:
   8 g Nutrient Broth (Difco Laboratories)
   1 L distilled water ($dH_2O$)
   Mix nutrient broth and water thoroughly, and autoclave at 121° C. for 15 minutes. Decant 15 mL portions into 50 mL centrifuge tubes.

2. M9 Media*:
   6 g $Na_2HPO_4$
   3 g $KH_2PO_4$
   1 g $NH_4Cl$
   0.5 g NaCl
   10 mL carbon source (eg. glucose, sucrose, trehalose, mannitol) (20%, w/v)
   1 mL $MgSO_4 \cdot 7H_2O$ (1M)
   1 mL Thiamine-HCl (0.1% w/v)
   1 mL 0.1M $CaCl_2$—$2H_2O$
   $dH_2O$ *(Atlas R., Park L. (Eds.) 1993. Handbook of Microbiological Media, CRC Press, Boca Raton, FL. USA p. 529)
   Combine $Na_2HPO_4$, $KH_2PO_4$, $NH_4Cl$, NaCl and bring volume to 987 mL using $dH_2O$. Autoclave 20 min and allow cool to room temperature. Aseptically add the rest of the sterilized M9 constituents.

3. REC Media*
   3.5 g $KH_2PO_4$
   5.0 g $K_2HPO_4$
   3.5 g $(NH_4)_2HPO_4$
   2 mL $MgSO_4 \cdot 7 H_2O$ [1 Molar] solution
   50 mL Glucose solution [20%, w/v]
   5 g Yeast Extract (optional)
   10 mL Trace metals stock solution (Table 1)

TABLE 1

Trace Metals Formulation (stock solution)

| Chemical | | g/100 mL |
|---|---|---|
| Ferric chloride - 6 hydrate | $FeCl_3 \cdot 6H_2O$ | 2.7 |
| Cobalt chloride - 6 hydrate | $CoCl_2 \cdot 6H_2O$ | 0.2 |
| Cupric sulfate - 5 hydrate | $CuSO_4 \cdot 5H_2O$ | 0.18 |

TABLE 1-continued

Trace Metals Formulation (stock solution)

| Chemical | | g/100 mL |
|---|---|---|
| Zinc sulfate - 7 hydrate | $ZnSO_4.7H_2O$ | 0.27 |
| Sodium molybdate | $NaMoO_4$ | 0.2 |
| Boric Acid | $H_3BO_4$ | 0.05 |
| Hydrochloric acid (12 M; 35%) | HCI | 10 mL |
| Distilled water | $H_2O$ | 100 mL |

*Fundamentals of Fermentation. Techniques for Benchtop Fermentors, 1996; Technical Paper, R & D Lab, new Brunswick Scientific Co., Inc., NJ, USA Combine $KH_2PO_4$, $K_2HPO_4$, $(NH_4)_2HPO_4$, and Yeast Extract into 1 L $dH_2O$. Autoclave for 20 minutes and let cool to <50° C. Aseptically add the rest of the sterilized REC constituents.

4. Pseudomonas-Agar F (PAF):
   35 g Pseudomonas-Agar F base (BDH)
   10 mL glycerol (Fisher)
   $dH_2O$
   Combine 35 g Pseudomonas-Agar F base together with 10 mL glycerol and bring to 1000 mL with $dH_2O$. Autoclave for 15 min at 15 psi at 121° C.
   The nutrient broth and M9 medium is prepared and autoclaved in 2 L culture bottles, and dispensed accordingly.

5. Phosphate Buffer:
   195 mL of 0.2 M stock solution comprising 31.2 g $NaH_2PO_4$ (Monobasic) per 1 L $dH_2O$.
   305 mL of 0.2 M stock solution comprising 53.65 g $Na_2HPO_4$-$7H_2O$ (Dibasic) per 1 L $dH_2O$.
   Mix the two solutions together and autoclave for 15 min at 15 psi at 121° C.

EXAMPLE 2

Bacterial Culturing

Rhizobacteria were originally isolated from roots of each weed species and grown on selective media. Single colonies of bacteria were inoculated into 15 mL nutrient broth in 50 mL centrifuge tubes and placed on a shaker for 48 h at 150 rpm and 15–20° C. The resulting culture was centrifuged for 6 minutes at 5400 rpm and the resulting supernatant was added to 0.9% Bacto agar at a concentration of 10–30% (v/v) and poured into sterile Petri dishes. Surface sterilized weed seeds were placed onto the agar (10 seeds/plate) and incubated at 15–20° C. for one week. Inoculated agar served as the control. Germination and root length were recorded (Kennedy, A. C., L. F. Elliott, F. L. Young and C. L. Douglas 1991. Rhizobacteria suppressive to the weed downy brome. Soil Sci. Soc. Am. J. 55:722–727.; and Boyetchko, S. M. 1997. Efficacy of rhizobacteria as biological control agents of grassy weeds. p. 460–462 in Proceedings of the Soils and Crop Works, Feb. 20–21, 1997., Saskatoon, Saskatchewan, Canada.). Twenty-five rhizobacterial isolates (for example, Pseudomonas spp. isolates) were re-tested in laboratory bioassays to examine their suppressive activity to green foxtail and wild oat.

Cultures of selected rhizobacterial strains, for example, BRG100, 189, BRG168 and OY4GFT9 are stored in 20% (w/w) glycerol in a −70° C. ultra-low freezer. An aliquot of the bacterial strain is transferred to Pseudomonas Agar-F (PAF) plates and incubated for 5 to 7 days at 15° C. Isolated colonies are inoculated into 15 mL of nutrient broth in 50 mL centrifuge tubes. After incubation at 15° C. for 48 hours on a rotary shaker at 150 rpm, the bacterial suspension is used as the seed culture for all subsequent treatments.

Erlenmeyer flasks (500 ml capacity) containing 250 ml of media (Example 1) are inoculated with 100 µl of the appropriate bacterial seed culture ($10^6$-$10^9$ cfu/mL). The uninoculated flasks served as the control. Cultures are grown at 15° at 150 rpm on a rotary shaker for 48 hours.

The bacterial concentrations are quantified by measuring the absorbance of the bacterial culture at 600 nm relative to culture medium minus the bacteria. Between readings, the spectrophotometer is flushed with 95% ethanol followed by distilled water, and then blanked with the corresponding uninoculated control flask. Duplicate absorbency readings (Absorbency A600 nm) are taken and the mean is used in all data analyses.

EXAMPLE 3

Monitoring Suppression of Weeds by Growth Pouch Bioassay

The suppression of weeds by biocontrol agents and biocontrol compositions is assessed using a growth pouch bioassay. Using this method a small volume of bacterial liquid culture grown in a nutrient liquid medium can be evaluated. Growth pouches (VWR-Canlab) are suspended in an acrylic box, seeds (surface sterilized in 10% bleach) of a plant to be tested are placed along the trough of each pouch and 20 ml of water is added to each pouch, dispensed between the plastic and paper wick to avoid disturbing seeds. The seeded pouches are maintained in the dark for 60±4 hrs at room temperature to initiate germination. Ten mL of a 10% Hoagland's solution is added, and seedlings inoculated using 2.0 ml of the bacterial culture suspension (REC media) distributed across the trough's length. Pouches are placed in a light cabinet (20° C.—16 h photoperiod; 15° C.—8 h dark period; relative humidity: 30–60%) within an hour of inoculation and incubated 6 to 7 days, after which time germination, root and shoot measurements (mm) are recorded. The root and shoot growth are recorded and the data is presented as percent suppression (compared to the appropriate uninoculated controls).

All experiments are conducted twice and consist of four replicates. Data for medium selection is analyzed by the Statistical Analysis System (SAS) using the analysis of variance (ANOVA) and General Linear Model (Proc GLM) procedure, and treatment means are separated using a Least Significant Difference (LSD) test (P=0.05).

Screening of Grass Species

Using the growth pouch bioassay several weed species, foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), green foxtail (*Setaria viridis*), and wild oat (*Avena fatua*) were tested for susceptibility to the biocontrol compositions of the present invention. The results below (Table 2) are the means of 2 experiments, 3 replications/experiment, unless otherwise indicated.

TABLE 2

Screening biocontrol compositions in Grass species

| Isolate | Mn. Rt. Lgth (mm)* | % Suppression |
|---|---|---|
| *Hordeum jubatum* (Foxtail barley): | | |
| Control | 40.2 ± 3.3 | |
| BRG100 | 15.9 ± 1.0 | 60% |
| BRG168 | 22.9 ± 2.3 | 43% |
| 189 | 14.1 ± 1.2 | 65% |
| OY4GFT9 | 42.9 ± 3.1 | — |
| *Digitaria sanguinalis* (Crabgrass): | | |
| Control | 21.3 ± 1.7 | |
| BRG100 | 4.9 ± 0.7 | 77% |
| BRG168 | 5.2 ± 0.8 | 76% |
| 189 | 6.3 ± 1.0 | 70% |
| OY4GFT9 | 7.8 ± 1.4 | 63% |
| *Lolium rigidum* (Annual rye grass): | | |
| Control | 71.8 ± 3.8 | |
| BRG100 | 22.5 ± 2.1 | 69% |
| BRG168 | 45.6 ± 5.3 | 36% |
| 189 | 27.5 ± 2.5 | 62% |
| OY4GFT9 | 35.8 ± 3.9 | 50% |
| *Echinochloa crusgalli* (Barnyard grass): | | |
| Control | 89.9 ± 3.6 | |
| BRG100 | 29.0 ± 3.9 | 68% |
| BRG168 | 39.3 ± 5.6 | 56% |
| 189 | 49.6 ± 4.2 | 45% |
| OY4GFT9 | 25.5 ± 4.1 | 72% |
| *Setaria glauca* (Yellow foxtail): | | |
| Control | 38.4 ± 2.9 | |
| BRG100 | 14.8 ± 1.7 | 61% |
| BRG168 | 18.2 ± 2.1 | 53% |
| 189 | 14.9 ± 1.4 | 61% |
| OY4GFT9 | 26.5 ± 2.8 | 31% |
| *Lolium multiflorum* (Italian rye grass): | | |
| Control | 48.2 ± 4.4 | |
| BRG100 | 17.0 ± 1.7 | 65% |
| BRG168 | 31.2 ± 4.1 | 35% |
| 189 | 19.2 ± 1.9 | 60% |
| OY4GFT9 | 41.7 ± 3.3 | 13% |
| *Setaria viridis* (UMDEL herbicide resistant green foxtail, group 3): | | |
| Control | 39.0 ± 5.2 | |
| BRG100 | 3.3 ± 0.6 | 92% |
| BRG168 | 10.0 ± 1.7 | 74% |
| 189 | 6.2 ± 0.7 | 84% |
| OY4GFT9 | 6.9 ± 1.0 | 82% |
| *Eleusine indica* (Goose grass): | | |
| Control | 5.6 ± 0.8 | |
| BRG100 | 4.1 ± 0.8 | 37% |
| BRG168 | 4.3 ± 1.5 | 23% |
| 189 | 5.5 ± 1.0 | 2% |
| OY4GFT9 | 4.2 ± 0.9 | 25% |

*mean root length

These results demostrate that suppression of growth, as determined by root length, was observed for each of foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), *Setaria viridis*, and wild oat (*Avena fatua*) using a variety of bacterial isolates.

EXAMPLE 4

Biocontrol Composition Field Assay

Dose response experiments are used to evaluate different application amounts of the formulated bacteria on weed suppression in the field. Bacteria are formulated in Pesta granules (U.S. Pat. No. 5,074,902; and Connick et al. 1991), or peat prills (Fravel et al. 1998).

Small plots (1 m$^2$) are staked out and weeds are seeded in 4 rows per m$^2$ plot. Pesta granules which contain about 7×10$^7$ cfu g$^{-1}$ bacteria, are applied (placed within furrow (below the weed seeds)) at three concentrations: 5 g row$^{-1}$, 10 g row$^{-1}$, and 50 g row$^{-1}$ which translate to concentrations of 20, 40, and 200 g m$^{-2}$ plot, respectively. For green foxtail, 100 seeds per row (400 seeds per m$^2$ plot) are sown in the soil. The seeding rate for wild oats is 40 seeds per row (160 seeds per m$^2$ plot). These seeding rates are based on average densities of weeds observed in the field. Weed emergence counts are made 4 and 8 weeks after application of the biocontrol composition and total aboveground biomass is determined after 8 weeks.

The results of these experiments are shown in FIGS. 1–6 and Table 3. The suppression of root and shoot growth of green foxtail by BRG100 and bacterial strain 189, in M9 medium and a nutrient broth medium are shown in FIGS. 1 and 2, respectively. Both bacterial strains result in the suppression of plant growth and development.

The suppression of root and shoot growth by BRG168 on wild oat when grown in M9 medium versus nutrient broth medium is shown in FIG. 3. BRG168 grown in both the nutrient broth and M9 medium suppresses root and shoot growth.

Bacterial strain BRG100 formulated in either peat prill and pesta is effective on green foxtail weed emergence at 4 and 8 weeks post application and on total weed biomass after 8 weeks (FIG. 4(A)). FIG. 4(B) depicts a pesta formulation of BRG100 on the suppression of green foxtail weed emergence and biomass, and demonstrates that various formulations of BRG100 may be used to suppress green foxtail weed emergence and reduce total weed biomass.

FIG. 4(C) depicts the efficacy of applying about 140 g/m$^2$ of pesta-formulated BRG100 at a different site from that used to collect data for FIGS. 4(A) and (B). Collectively, FIGS. 4(A)–(C), demonstrated that BRG100 is capable of suppressing green foxtail weed emergence and reducing total weed biomass under varying field conditions.

This data indicate that bacterial strain BRG100 may be used for the suppression of green foxtail growth.

Referring to FIGS. 5(A) and 5(B), there is shown the effect of bacterial strain 189 in peat prill formulations on green foxtail weed emergence in the field at 4 and 8 weeks post application and on total weed biomass after 8 weeks post application. FIG. 5(A), shows that bacterial strain 189 applied as a peat prill formulation suppresses the emergence of green foxtail weed and reduces its biomass. The results demonstrate that bacterial strain 189 may be used to suppresses the emergence, and reduce the biomass, of green foxtail.

FIG. 5(B) compares the efficacy of bacterial strain 189 against that of BRG100 for suppression of green foxtail weed emergence and biomass following an application of 140 g/m$^2$ of the respective bacteria in a peat prill biocontrol composition. The results indicate that bacterial strain 189 and BRG100 are similar in their abilities to suppress the emergence and biomass of green foxtail.

Therefore, the present invention provides for the use of bacterial strain 189 formulated in a suitable composition for the suppression of green foxtail growth.

Referring to FIGS. 6(A) and (B), there is shown the effect of bacterial strain BRG168 is in peat prill and pesta formulation on wild oat weed emergence at 4 and 8 weeks post application and on total weed biomass at 8 weeks post application. FIG. 6(A), indicates that a peat prill biocontrol composition of BRG168 suppresses the emergence, and reduces the biomass, of wild oat weed. FIG. 6(B) depicts the suppression of wild oat weeds following an application of BRG168 formulated in peat prills and applied at about 140 g/m² at a second site from the location where the results for FIG. 6(A) were obtained. FIG. 6(B) demonstrates that bacterial strain BRG168 is capable of suppressing wild oat weed emergence and biomass, and collectively, FIGS. 6(A) and 6(B) demonstrate that bacterial strain BRG168 is effective under varying field conditions.

Field Results Using BRG100

Field results using BRG100 as a controlling agent for green foxtail is shown in Tables 3 and 4 (two different growing seasons).

At the time of application of the biocontrol agent in the field in the first season, enumeration of pesta formulation indicated that there were $7.2 \times 10^7$ cfu/gram of formulation with BRG100. The soil conditions during this growing season were extremely dry at both Saskatoon and Scott, but Saskatoon had drier soil conditions.

TABLE 3

Efficacy of Bacterial Strain BRG100 for
Control of Green Foxtail using Pesta Formulation.

| Treatment | Emergence | | Biomass | |
|---|---|---|---|---|
| | No. of Plants | % Suppression | Weight(g) | % Suppression |
| Saskatoon Research Farm: | | | | |
| 0 g  4 wks | 219251 | — | — | |
|     8 wks | — | | 145 | — |
| 20 g 4 wks | 120133 | 4547 | | |
|     8 wks | | | 92 | 37 |
| 40 g 4 wks | 86102 | 6159 | | |
|     8 wks | | | 90 | 38 |
| 200 g 4 wks | 5666 | 7474 | | |
|     8 wks | | | 64 | 56 |
| Scott Experimental Farm: | | | | |
| 0 g  4 wks | 205213 | — | | |
|     8 wks | | — | 189 | — |
| 140 g 4 wks | 2037 | 90 | | |
|     8 wks | | 83 | 32 | 83 |

Field results in shown in Table 3 were obtained during a season of low soil moisture and poor soil contact at time of seeding. Under these conditions, at Saskatoon, up to 74% weed control at the high rate of application (50 g/row; 200 g total) after 4 and 8 weeks was achieved. In addition, even at the lower rates of application, weed control was very good: 45% and 47% after 4 and 8 weeks, respectively, at a rate of 5 g/row (20 g total), and 61% and 59% after 4 and 8 weeks, respectively, at a rate of 10 g/row (40 g total). Aboveground biomass was reduced by 37%, 38%, and 56% at rates of 5, 10, and 50 g/row, respectively, after 8 weeks.

At the Scott Experimental Farm, reduction in weed emergence after 4 and 8 weeks were 90% and 83%, respectively, at a rate of 35 g/row (140 g total) was also observed. Also, aboveground biomass was reduced by 83%.

These data indicate that the amount of bacteria (i.e. titer) contained in the formulation and sampling of the bacteria at a later growth stage (late stationary phase) may result in a greater amount of weed control. Furthermore, these data suggest that encapsulation of the bacteria into the pesta formulation may be advantageous.

Field results were repeated and these results are shown in Table 4. For this experiment, enumeration of bacterial populations of strain BRG100, determined at the time of application in the field, indicated that there were $9.3 \times 10^8$ cfu/g with strain BRG100. Extreme drought conditions and delayed weed emergence were observed at the Saskatoon site.

TABLE 4

Efficacy of Bacterial Strain BRG100 for Control of
Green Foxtail using Pesta Formulation Alternate Field Season

| Treatment | Emergence | | Biomass | |
|---|---|---|---|---|
| | No. of Plants | % Suppression | Weight (g) | % Suppression |
| Saskatoon Research Farm: | | | | |
| 0 g 10 wks | 94101 | — | −5.2 | |
|    12 wks | — | | | — |
| 4 g 10 wks | 97120 | 0 | −4.9 | |
|    12 wks | | | | 5.8 |
| 20 g 10 wks | 90 | 50 | −5.6 | |
|    12 wks | 111 | | | 0 |
| 40 g 10 wks | 319104 | 150 | −4.7 | |
|    12 wks | | | | 9.7 |
| 200 g 10 wks | 28779 | 2421 | −3.5 | |
|    12 wks | | | | 32.7 |
| Scott Experimental Farm: | | | | |
| 0 g  4 wks | 255286 | — | −265 | |
|     8 wks | — | | | — |
| 4 g  4 wks | 217235 | 1518 | −217 | |
|     8 wks | | | | 18 |
| 40 g 4 wks | 75 | 7068 | −125 | |
|     8 wks | 93 | | | 53 |
| 140 g 4 wks | 4955 | 8181 | −84 | |
|     8 wks | | | | 68 |

For bacterial strain BRG100, field results were much superior at the Scott site than at the Saskatoon site (Table 4). Despite the drought conditions at the Saskatoon site, BRG100 was able to reduce weed emergence after 10 and 12 weeks by 24% and 21%, respectively, at a rate of 50 g/row. There was some reduction in weed emergence at the lower rates of application after 10 weeks. Total aboveground biomass was reduced up to 32.7% at the highest rate of application.

At the Scott site (Table 4), where the seasonal rainfall was better (than the Saskatoon site), reductions in weed emergence were 18%, 68%, and 81% at rates of 1, 10, and 35% g/row after 8 weeks. Reductions in weed emergence after 4 weeks were similar. Aboveground biomass was reduced by 18%, 53%, and 68% at rates of 1, 10, and 35 g/row.

Despite the lower weed biocontrol values at the Saskatoon site, the fact that weed suppression occurred after 10 to 12 weeks under drought conditions indicates that the bacteria can provide residual weed biocontrol throughout the growing season. This may provide opportunities for controlling weeds using a biocontrol composition, even when the window of opportunity to spray with post-emergent chemical herbicides in a cropping system is past.

Even though reduced emergence of weeds in some cases were not high, individual plants were smaller in plots treated with bacteria. This observation is also supported by high reductions in aboveground biomass. It should be noted that higher levels of bacterial populations in each gram of formulation, results in weed biocontrol activity at rates of 1 and 5 g/row (Table 4, Scott Experimental Farm)

Field Results Using Bacterial Strain 189

At the time of application in the field, enumeration of bacterial populations of strain 189 in pesta formulation indicated that there were $1.9 \times 10^8$ cfu/g for strain 189. This field season was characterised with extreme drought conditions at the Saskatoon site, resulting in delayed weed emergence by several weeks. At the Scott site, precipitation in the spring was below average, however, the level of soil moisture was greater than at the Saskatoon site. The results are shown in Table 5.

TABLE 5

Efficacy of Bacterial Strain 189 for Control of
Green Foxtail Using Pesta Formulation Alternate Field Season

| Treatment | Emergence | | Biomass | |
|---|---|---|---|---|
| | No. of Plants | % Suppression | Weight(g) | % Suppression |
| Saskatoon Research Farm: | | | | |
| 0 g  10 wks | 97132 | — | −44 | — |
| 12 wks | — | | | — |
| 4 g  10 wks | 94106 | 320 | −33 | |
| 12 wks | | | | 25 |
| 20 g  10 wks | 84107 | 1419 | −28 | |
| 12 wks | | | | 35 |
| 40 g  10 wks | 84113 | 1414 | −23 | |
| 12 wks | | | | 46 |
| 200 g  10 wks | 5985 | 3936 | −11 | |
| 12 wks | | | | 75 |
| Scott Experimental Farm: | | | | |
| 0 g  4 wks | 255286 | | | |
| 8 wks | | — | 265 | — |
| 4 g  4 wks | 188207 | 2627 | −207 | |
| 8 wks | | | | 22 |
| 40 g  4 wks | 119 | 53 | — | |

For bacterial strain 189, at the Saskatoon site, weed emergence was reduced by 20%, 19%, 14%, and 36% at rates of 1, 5, 10, and 50 g/row after 12 weeks (4, 20, 40 and 200 g, respectively; Table 5). Aboveground biomass was reduced by 25%, 35%, 46%, and 75% at these same rates of application. Even though reductions in weed emergence were lower than aboveground biomass, the plants that emerged were smaller and less vigorous, often due to the effects of the bacterial agent on seedling vigor and delays in weed emergence.

At the Scott site, weed emergence was reduced by 27% and 59% at rates of 1 and 10 g/row, respectively, after 8 weeks (4 and 40 g, respectively; Table 5). Aboveground biomass was also reduced by 22% and 44% at these same rates.

Despite the lower weed biocontrol values at the Saskatoon site (similar to those found for BRG100 in Table 4), weed suppression was observed after 10 to 12 weeks under drought conditions, indicating that the bacteria can provide residual weed biocontrol throughout the growing season. Therefore, as observed for BRG100, it may be possible to control these weeds when the window of opportunity to spray with post-emergent chemical herbicides in a cropping system is long past.

Due to a high quality of active ingredient and high levels of bacterial populations in each gram of formulation, weed biocontrol activity is demonstrated at rates of 1 and 5 g/row (4 or 20 g, respectively, Table 5).

These data collectively demonstrate that low dose of a biocontrol agent comprising a sufficient titre of agent, may be applied under field conditions and provide effective weed control activity.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. An isolated biocontrol agent comprising, at least one Pseudomonas strain selected from the group consisting of bacterial strains BRG100 (IDAC 141200-1), BRG168 (IDAC 141200-2), 189 (IDAC 141200-3), OY4GFT9 (IDAC 141200-5) and a combination of the preceding.

2. The isolated biocontrol agent of claim 1, where the biocontrol agent is bacterial strain BRG100 (IDAC 141200-1).

3. The isolated biocontrol agent of claim 1, where the biocontrol agent is bacterial strain BRG168 (IDAC 141200-2).

4. The isolated biocontrol agent of claim 1, where the biocontrol agent is bacterial strain 189 (IDAC 141200-3).

5. The isolated biocontrol agent of claim 1, where the biocontrol agent is bacterial strain OY4GFT9 (IDAC 141200-5).

6. A biocontrol composition comprising the biocontrol agent of claim 1 in an acceptable medium.

7. The biocontrol composition of claim 6, where the acceptable medium comprises one or more than one of the group consisting of a liquid culture medium, a solid culture medium, a seed coating, pesta, peat prill, vermiculite, clay, starch and wheat straw.

8. The biocontrol composition of claim 6, wherein the acceptable medium is pesta.

9. The biocontrol composition of claim 6, wherein the acceptable medium is peat prill.

10. The biocontrol composition of claim 6, wherein the acceptable medium comprises one or more than one of the group consisting of a liquid culture medium, a solid culture medium, a seed coating, pesta, peat prill, vermiculite, clay, starch and wheat straw.

11. The biocontrol composition of claim 10, where the acceptable medium is pesta.

12. The biocontrol composition of claim 10, where the acceptable medium is peat prill.

13. The biocontrol composition of claim 10, where the at least one Pseudomonas strain is bacterial strain BRG100 (IDAC 141200-1).

14. The biocontrol composition of claim 6, where the at least one Pseudomonas strain is BRG168 (IDAC 141200-2).

15. The biocontrol composition of claim 6, where the at least one Pseudomonas strain is 189 (IDAC 141200-3).

16. The biocontrol composition of claim 6, where the at least one Pseudomonas strain is OY4GFT9 (IDAC 141200-5).

17. A method for suppressing weed growth comprising applying the isolated biocontrol agent of claim 1 to a weed, where the weed is selected from the group consisting of green foxtail (*Setaria viridis* [L.] Beauv.), foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), and wild oat (*Avena fatua*).

18. A method for suppressing weed growth comprising applying the isolated biocontrol agent of claim 6 a weed, where the weed is selected from the group consisting of green foxtail (*Setaria viridis* [L.] Beauv.), foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), and wild oat (*Avena fatua*).

19. A method of suppressing one or more than one weed selected from the group consisting of green foxtail (*Setaria*

*viridis* [L.] Beauv.), foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), and wild oat (*Avena fatua*) during crop growth comprising;

a) adding an effective amount of the biocontrol agent of claim, to soil to produce a treated soil;
 b) planting crops in the treated soil; and
 c) growing the crops.

20. A method of suppressing one or more weeds selected from the group consisting of green foxtail (*Setaria viridis* [L.] Beauv.), foxtail barley (*Hordeum jubatum*), crabgrass (*Digitaria sanguinalis*), annual ryegrass (*Lolium rigidum*), barnyard grass (*Echinochloa crusgalli*), yellow foxtail (*Setaria glauca*), Italian rye grass (*Lolium multiflorum*), Goose grass (*Eleusine indica*), and wild oat (*Avena fatua*) during crop growth comprising;

a) adding an effective amount of the biocontrol composition according to claim 6 to soil to produce a treated soil;
 b) planting crops in the treated soil; and
 c) growing the crops.

* * * * *

UNITED STATES PATENT AND TRADEMARK OFFICE
CERTIFICATE OF CORRECTION

PATENT NO. : 6,881,567 B2
DATED : April 19, 2005
INVENTOR(S) : Susan M. Boyetchko, Karen Sawchyn and Jon Geissler It is certified that error appears in the above-identified patent and that said Letters Patent is hereby corrected as shown below:

<u>Title page,</u>
Item [73], Assignee, replace "Her Majesty the Queen in Right of Canada as Represented by the Minister of Agricultural and Agri-Food Canada" with:
-- Her Majesty the Queen in Right of Canada as represented by the Minister of Agriculture and Agri-Food Canada --.

Signed and Sealed this

Fifth Day of July, 2005

JON W. DUDAS
*Director of the United States Patent and Trademark Office*

UNITED STATES PATENT AND TRADEMARK OFFICE
CERTIFICATE OF CORRECTION

PATENT NO.   : 6,881,567 B2
DATED        : April 19, 2005
INVENTOR(S)  : Susan M. Boyetchko, Karen Sawchyn and Jon Geissler It is certified that error appears in the above-identified patent and that said Letters Patent is hereby corrected as shown below:

Title page,
Item [56], References Cited, OTHER PUBLICATIONS:
"Connick, Jr., W.J. et al., "Shelf" reference, change "*Colletotrichum trunactum*" to -- *Colletotrichum truncatum* --.
"Kremer" reference, change "Weed Seedings" to -- Weed Seedlings --.

Column 2,
Line 53, change "*Pseudomonas synringae*" to -- *Pseudomonas syringae* --.

Column 5,
Line 15, change "All reference cited" to -- All references cited --.

Column 7,
Line 12, change "(*Lolium multiforum*)" to -- (*Lolium multiflorum*) --.
Lines 14 and 33, change "(*Avena fauta*)" to -- (*Avena fatua*) --.

Column 9,
Lines 10 and 42, change "Result from field trails" to -- Results from field trials --.
Line 59, delete "weed".
Line 60, delete "weeds".

Column 10,
Line 41, change "1 mL 0.1M $CaCl_2$—$2H_2O$" to -- 1 mL 0.1M $CaCl_2.2H_2O$ --.

Column 11,
Line 31, change "$NaH_2PO_4$" to -- NaH2PO$_4$.$2H_2O$ --.
Line 50, change "inoculated" to -- uninoculated --.

Column 14,
Line 39, change "This data" to -- These data --.
Line 62, delete "and pesta".

UNITED STATES PATENT AND TRADEMARK OFFICE
CERTIFICATE OF CORRECTION

PATENT NO. : 6,881,567 B2
DATED : April 19, 2005
INVENTOR(S) : Susan M. Boyetchko, Karen Sawchyn and Jon Geissler It is certified that error appears in the above-identified patent and that said Letters Patent is hereby corrected as shown below:

<u>Column 15,</u>
Lines 20-41, replace Table 3 with the following:

Table 3

Efficacy of Bacterial Strain BRG100 for
Control of Green Foxtail using Pesta Formulation

| Treatment | | Emergence | | Biomass | |
|---|---|---|---|---|---|
| | | No. of Plants | % Suppression | Weight | % Suppression |
| Sakatoon Research Farm: | | | | | |
| 0 g | 4wks | 219 | --- | | |
| | 8wks | 251 | --- | 145 | --- |
| 20 g | 4wks | 120 | 45 | | |
| 40 g | 8wks | 133 | 47 | 92 | 37 |
| 200 g | 4wks | 86 | 61 | | |
| | 8wks | 102 | 59 | 90 | 38 |
| 0 g | 4wks | 56 | 74 | | |
| 140 g | 8wks | 66 | 74 | 64 | 56 |
| Scott Experimental Farm: | | | | | |
| 0 g | 4wks | 205 | --- | | |
| | 8wks | 213 | --- | 189 | --- |
| 140 g | 4wks | 20 | 90 | | |
| | 8wks | 37 | 83 | 32 | 83 |

Line 43, change "Field results in shown in Table 3" to -- Field results shown in Table 3 --.

UNITED STATES PATENT AND TRADEMARK OFFICE
CERTIFICATE OF CORRECTION

PATENT NO.    : 6,881,567 B2
DATED         : April 19, 2005
INVENTOR(S)   : Susan M. Boyetchko, Karen Sawchyn and Jon Geissler It is certified that error appears in the above-identified patent and that said Letters Patent is hereby corrected as shown below:

<u>Column 16,</u>
Lines 5-33, replace Table 4 with the following:

Table 4

Efficacy of Bacterial Strain BRG100 for
Control of Green Foxtail using Pesta Formulation Alternate Field Season

| Treatment | | Emergence | | Biomass | |
|---|---|---|---|---|---|
| | | No. of Plants | % Suppression | Weight | % Suppression |
| Sakatoon Research Farm: | | | | | |
| 0 g | 10wks | 94 | --- | --- | --- |
|  | 12wks | 101 | --- | 5.2 | --- |
| 4 g | 10wks | 97 | 0 | --- | --- |
|  | 12wks | 120 | 0 | 4.9 | 5.8 |
| 20 g | 10wks | 90 | 5 | --- | --- |
|  | 12wks | 111 | 0 | 56 | 0 |
| 40 g | 10wks | 319 | 15 | --- | --- |
|  | 12wks | 104 | 0 | 4.7 | 9.7 |
| 200 g | 10wks | 287 | 24 | --- | --- |
|  | 12wks | 79 | 21 | 3.5 | 32.7 |
| Scott Experimental Farm: | | | | | |
| 0 g | 4wks | 255 | --- | --- | --- |
|  | 8wks | 286 | --- | 265 | --- |
| 4 g | 4wks | 217 | 15 | --- | --- |
|  | 8wks | 235 | 18 | 217 | 18 |
| 40 g | 4wks | 75 | 70 | --- | --- |
|  | 8wks | 93 | 68 | 125 | 53 |
| 140 g | 4wks | 49 | 81 | --- | --- |
|  | 8wks | 55 | 81 | 84 | 68 |

UNITED STATES PATENT AND TRADEMARK OFFICE
CERTIFICATE OF CORRECTION

PATENT NO.    : 6,881,567 B2
DATED         : April 19, 2005
INVENTOR(S)   : Susan M. Boyetchko, Karen Sawchyn and Jon Geissler It is certified that error appears in the above-identified patent and that said Letters Patent is hereby corrected as shown below:

Column 17,
Lines 7-30, replace Table 5 with the following:

Table 5

Efficacy of Bacterial Strain 189 for Control of
Green Foxtail using Pesta Formulation Alternate Field Season

| Treatment | | Emergence | | Biomass | |
|---|---|---|---|---|---|
| | | No. of Plants | % Suppression | Weight | % Suppression |
| Saskatoon Research Farm: | | | | | |
| 0 g | 10wks | 97 | --- | --- | --- |
| | 12wks | 132 | --- | 44 | --- |
| 4 g | 10wks | 94 | 3 | --- | |
| | 12wks | 106 | 20 | 33 | 25 |
| 20 g | 10wks | 84 | 14 | --- | |
| | 12wks | 107 | 19 | 28 | 35 |
| 40 g | 10wks | 84 | 14 | --- | |
| | 12wks | 113 | 14 | 23 | 46 |
| 200 g | 10wks | 59 | 39 | --- | |
| | 12wks | 85 | 36 | 11 | 75 |
| Scott Experimental Farm: | | | | | |
| 0 g | 4wks | 255 | | | |
| | 8wks | 286 | --- | 265 | --- |
| 4 g | 4wks | 188 | 26 | --- | |
| | 8wks | 207 | 27 | 207 | 22 |
| 40 g | 4wks | 119 | 53 | --- | |
| | 8wks | 118 | 59 | 148 | 44 |

Signed and Sealed this

Sixth Day of September, 2005

JON W. DUDAS
*Director of the United States Patent and Trademark Office*